(12) United States Patent
Wang

(10) Patent No.: US 8,148,143 B2
(45) Date of Patent: *Apr. 3, 2012

(54) METHOD AND COMPOSITION FOR GENETICALLY MODIFYING NON-HUMAN CELLS AND ANIMALS

(75) Inventor: Kangsheng Wang, Hacienda Heights, CA (US)

(73) Assignee: Kwang-Hua Development and Investment Ltd., Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 12/036,198

(22) Filed: Feb. 22, 2008

(65) Prior Publication Data

US 2009/0133134 A1 May 21, 2009

Related U.S. Application Data

(63) Continuation-in-part of application No. 11/407,851, filed on Apr. 20, 2006, now abandoned, which is a continuation of application No. 11/372,241, filed on Mar. 9, 2006, now abandoned, and a continuation of application No. 09/537,861, filed on Mar. 28, 2000, now Pat. No. 7,067,308, said application No. 11/372,241 is a continuation of application No. 09/781,046, filed on Feb. 8, 2001, now Pat. No. 7,053,187, which is a continuation-in-part of application No. 09/537,861.

(51) Int. Cl.
| | |
|---|---|
| *C12N 15/00* | (2006.01) |
| *C12N 5/00* | (2006.01) |
| *C12N 5/02* | (2006.01) |
| *C07K 16/00* | (2006.01) |

(52) U.S. Cl. .............. 435/320.1; 435/325; 435/455; 530/387.1; 530/388.1; 800/21; 800/25

(58) Field of Classification Search .............. 435/320.1, 435/325, 455; 530/387.1, 388.1; 800/21, 800/25

See application file for complete search history.

(56) References Cited

U.S. PATENT DOCUMENTS

| | | | |
|---|---|---|---|
| 5,428,132 A | 6/1995 | Hirsch et al. | |
| 5,521,291 A | 5/1996 | Curiel et al. | |
| 5,744,335 A | 4/1998 | Wolff et al. | |
| 6,045,786 A * | 4/2000 | Cone et al. | 424/78.02 |
| 6,063,630 A | 5/2000 | Treco et al. | |
| 7,053,187 B2 | 5/2006 | Wang | |
| 7,067,308 B1 | 6/2006 | Wang | |

FOREIGN PATENT DOCUMENTS

| | | |
|---|---|---|
| CN | 1208600 | 2/1999 |
| EP | 0431839 B1 | 6/1991 |
| EP | 0867114 A1 | 9/1998 |
| EP | 0846772 A1 | 10/1998 |
| RU | 2081914 | 6/1997 |
| WO | WO 90/08192 | 7/1990 |
| WO | WO 93/24626 | 12/1993 |
| WO | WO 97/11597 | 4/1997 |
| WO | WO 99/38991 | 8/1999 |
| WO | WO 99/40213 | 8/1999 |
| WO | WO 99/42569 | 8/1999 |
| WO | WO 00/08924 | 2/2000 |
| WO | WO 00/29602 | 5/2000 |
| WO | WO 01/73094 A2 | 10/2001 |

OTHER PUBLICATIONS

Kuby. Immunology, Third Edition, pp. 131-134, 1997.*
Alberts et al. Mol. Biol. of the Cell, 3rd Ed. pp. 1216-1220, 1994.*
Anwer, K. et al., "Targeted Gene Delivery: A Two-Pronged Approach", Critical Reviews in Therapeutic Drug Carrier Systems 17:377-424 (2000).
Bain, G., et al., "Embryonic Stem Cells Express Neuronal Properties In Vitro," Developmental Biology 168:342-357 (1995).
Barker, R. A., et al., "Preparation of Cell Suspensions for Transplantation," Neuromethods 36:195-205.
Barnes, F. L. et al., "Blatocyst Development and Birth After In-Vitro Maturation of Human Primary Oocytes, Intracytoplasmic Sperm Injection and Assisted Hatching," Human Reproduction, 10:3243-3247 (1995).
Birnstiel, M., et al., "Dangerous Liaisons: Spermatozoa as Natural Vectors for Foreign DNA?," Cell 57: 701-702 (1989).
Bohn, M. C. et al., "Gene Therapies for Parkinson's Disease," Gene Therapy for Neurological Disorders and Brain Tumors, pp. 377-395.
Bookbinder, L. H. et al., "Tissue- and Species-Specific Express of sp56, a Mouse Sperm Fertilization Protein," Science 269:86-89 (1995).
Brackett, et al., "Uptake of Heterologous Genome by Mammalian Spermatozoa and Its Transfer to Ova Through Fertilization," PNAS 68:353-357 (1971).
Brinster, R. L., et. al., "No Simple Solution for Making Transgenic Mice," Cell 59:239-241 (1989).
Burks, D. J. et al., "Interaction of a Tyrosine Kinase from Human Sperm with the Zona Pellucida at Fertilization," Science 269:83-86 (1995).

(Continued)

*Primary Examiner* — Thaian N Ton
(74) *Attorney, Agent, or Firm* — Knobbe Martens Olson & Bear LLP

(57) ABSTRACT

A vector and its use to generate genetically modified animals and cells is disclosed. One aspect involves a vector that comprises a sperm cell and one or more polynucleotide molecules bound to a sperm cell through one or more anti-sperm antibody linker. In one preferred embodiment, the one or more polynucleotide molecules encode for a gene product that confers desired characteristics in the cells or the animals. In another preferred embodiment, the genetically modified cells are able to produce desired therapeutic proteins. The association of the sperm, linker, and the one or more polynucleotide can occur in vitro or in vivo. In another embodiment, the genetically modified cells are transgenic chicken eggs in which one or more desired recombinant protein is expressed. In another aspect, genetically modified cells or animals are derived form the fertilization of an animal egg call with the vector described above. Another aspect includes cells, such as sperm cells or egg cells, and cell lines that are derived from these genetically modified animals or their descendants.

6 Claims, 16 Drawing Sheets

OTHER PUBLICATIONS

Carballada, R., "Regulation of Foreign DNA Uptake by Mouse Spermatozoa," Exp. Cell Research 262:104-113 (2001).
Castro, A. J., et al., "Neural Transplantation in the Developing CNS," Neuromethods 36:169-194.
Chandran, S., et al., "Neural Stem Cells for Transplantation," Neuromethods 36:41-54.
Chang, I. K. et al., "Production of Germline Chimeric Chickens by Transfer of Cultured Primordial Germ Cells," Cell Biology International 21:495-499 (1997).
Chang, K., et al., "Effective Generation of Transgenic Pigs and Mice by Linker Based Sperm-Mediated Gene Transfer", BMC Biotechnology (2002), 2:5, http://www.biomedcentral.com/1472-6750/2/5.
Cheng, A., et al., "Sperm-Egg Recognition in the Mouse: Characterization of sp56, A Sperm Protein Having Specific Affinity for ZP3", The Journal of Cell Biology 125:867-878 (1994).
Cornwall, G. A., et al., "Inhibition of the Mouse Sperm Surface α-D-Mannosidase Inhibits Sperm-Egg Binding in Vitro," Biology of Reproduction 44:913-921 (1991).
Cozzi, E., et. al., "Expression of Human Decay Accelerating Factor in Transgenics Pigs," Transplantation Proceedings 26:1402-1403 (1994).
Davar, G., "Gene Therapy for Pain," Gene Therapy for Neurological Disorders and Brain Tumors, pp. 419-426.
Dickson, D., "Dangerous' Liasons in Cell Biology," Science 244:1539-1540 (1989).
Dunnett, S. B., et al., "Basic Transplantation Methods in Rodent Brain," Neuromethods 36:133-148.
Etherton, T. D., et. al., "Mechanism by Which Somatotropin Decreases Adipose Tissue Growth," Am. J. Clin. Nutrition 58:287S-295S (1993).
Fernandez, M. A., et al., "Sperm-Mediated Gene Transfer Into Oocytes of the Golden Hamster: Assessment of Sperm Function," Indian J. Exp. Biol. 37:1085-1092 (1999).
Francolini, M., et. al., "Evidence for Nuclear Internalization of Exogenous DNA into Mammalian Sperm Cells," Mol. Reprod. Devel. 34:133-139 (1993).
Fusi, F. M., "In Vitro Production of Human Anti-Sperm Antibodies: Effect of an Oligoclonal Antibody (F6) on Sperm-Egg Interaction," J. Reprod. Immun. 29:135-147 (1995).
Gagne, M. B., et. al., "Electroporation of Bovine Spermatozoa to Carry Foreign DNA in Oocytes," Mol. Rep. Devel. 29:6-15 (1991).
Gandolfi, F., "Sperm-Mediated Transgenesis," Theriogenology 53:127-137 (2000).
Gandolfi, F., "Spermatozoa, DNA Binding and Transgenic Animals," Transgenic Res. 7:147-155 (1998).
Gao, Z., et al., "Species Diversity in the Structure of Zonadhesin, a Sperm-specific Membrane Protein Containing Multiple Cell Adhesion Molecule-like Domains," J. Biol. Chem. 273:3415-3421 (1998).
Gardner, D. K., et al., "Culture and Selection of Viable Blastocysts: a Feasible Proposition for Human IVF?," Human Reproduction Update 3:367-382 (1997).
Gardner, D. K., et al., "Culture and Transfer of Human Blastocysts Increases Implantation Rates and Reduces the Need for Multiple Embryo Transfers," Fertility and Sterility 69:84-88 (1998).
Gougoulidis, T., et al., "Inhibition of Bovine Sperm-Oocyte Fusion by the Carbohydrate GalNAc", Mol. Rep. & Devel. 54:179-185 (1999).
Hardy, D. M., et al., "A Sperm Membrane Protein That Binds in a Species-Specific Manner to the Egg Extracellular Matrix Is Homologous to von Willebrand Factor," J. Biol. Chem. 270:26025-26028 (1995).
Hasebe, M., et. al. "An Attempt to Produce Transgenic Chicken Mediating Sperm Cells as Vectors," J. Applied Animal Res. 14:143-150 (1998).
Histocompatibility: Interpretation and Correlation of HLA Typing for Bone Marrow Transplantation. http://www.bmtinfo.org/bmt/topics/htm/type_b.htm. Oct. 24, 2000, pp. 1-9.
Huard, J., et al., "Gene Transfer to Muscle and Spinal Cord Using Herpes Simplex-Based Virus," Stem Cell Biology and Gene Therapy pp. 179-200 (1998).

Human embryonic stem cell and embryonic germ cell lines. http://www.ncbi.nlm.nih.gov/entrez/query.fcgi?cmd=Retrieve&db-PubMed&list_uids-10.6. Oct. 25, 2000, p. 1.
Hurley, C. K., et al., "HLA Typing by Molecular Methods," Manual of Clinical Laboratory Immunology 140:1098-1111 (1997).
International Search Report for PCT International Application No. PCT/US01/07018, dated Dec. 3, 2002, 5 pages.
International Search Report for PCT International Application No. PCT/US02/02895, dated Oct. 7, 2003, 7 pages.
International Search Report for PCT International Application No. PCT/US02/40492, dated Jun. 5, 2003, 4 pages.
Isacson, O., et al., "Gene Therapy of Huntington's Disease," Gene Therapy for Neurological Disorders and Brain Tumors, pp. 427-443.
Isolation of a primate embryonic stem cell line. http://www.ncbi.nlm.nih.gov/entrez/query.fcgi?cmd-Retrieve&db-PubMed&list_uids-75.4. Oct. 25, 2000, pp. 1-2.
Kadam, A. L., et al., "Fertilization Antigen (FA-1) Completely Blocks Human Sperm Binding to Human Zona Pellucida: FA-1 Antigen May be a Sperm Receptor for Zona Pellucida in Humans", Journal of Reproductive Immunology 29:19-30 (1995).
Kalab, P., et al., "p95, the Major Phosphotyrosine-Containing Protein in Mouse Spermatozoa, Is a Hexokinase with Unique Properties", J. Biol. Chem. 269:3810-3817 (1994).
Kameda, K., et al., "Comparative Studies of the Antigens Recognized by Sperm-Immobilizing Monoclonal Antibodies", Biology of Reproduction 46:349-357 (1992).
Katovich, H., et al., "Histocompatibility: Interpretation and Correlation of HLA Typing for Bone Marrow Transplantation," http://www.bminfo.org/bmt/topics/htm/dnatype.htm, Oct. 24, 2000, pp. 1-12.
Kaye, E. M., "Gene Therapy for Lysosomal Storage Diseasese," Gene Therapy for Neurological Disorders and Brain Tumors, pp. 409-418.
Kim, et al., "Effects of Experimentally Generated Bull Antisperm Antibodies on in Vitro Fertilization," Biology of Reproduction 60:1285-1291 (1999).
Kinu, K., et al., "Comparative Studies of the Antigens Recognized by Sperm-Immobilizing Monoclonal Antibodies," Bio. of Reprod. 46:349-357 (1992).
Klug, M. G., et al., "Genetically Selected Cariomyocytes from Differentiating Embryonic Stem Cells From Stable Intracardiac Grafts," J. Clin. Invest. 98:216-224 (1996).
Kolosov, E., et al., "Functional Characteristics of ES Cell-derived Cardiac Precursor Cells Identified by Tissue-specific Expression of the Green Fluorescent Protein," J. Cell Biol. 143:2045-2056 (1998).
Lacy, H. M., et al., "Sperm Protein 17 is Expressed on Normal and Malignant Lymphocytes and Promotes Heparin Sulfate-Mediated Cell-Cell Adhesion," Blood 98:2160-2165 (2001).
Lavitrano, M., et. al., "Human Decay Accelerating Factor Transgenic Pigs Obtained by Sperm Mediated Gene Transfer," Transplantation Proceedings 31:972-974 (1999).
Lavitrano, M., et. al., "Sperm Cells as Vectors for Introducing Foreign DNA into Eggs: Genetic Transformation of Mice," Cell 57:717-723 (1989).
Lavitrano, M., et. al., "The Interaction Between Exogenous DNA and Sperm Cells," Mol. Reprod. Devel. 31:161-169 (1992).
Li, M., et al., "Generation of Purified Neural Precursors from Embryonic Stem Cells by Lineage Selection," Current Biology vol. 8, No. 17 (1998).
Liu, X. Y., et. al., "Association of Foreign DNA with Sperm of Gilthead Seabream, Sparus aurata, After Sonication, Freezing, and Dimethyl Sulfoxide Treatments," Marine Biotech. 1:175-183 (1999).
Lonnerdal, B., "Recombinant Human Milk Proteins—An Opportunity and a Challenge," Am. J. Clin. Nutrition 63:622-626 (1996).
Lu, Q., et al., "Sperm from β1,4-Galactosyltransferase-Null Mice are Refractory to ZP3-Induced Acrosome Reactions and Penetrate the Zona Pellucida Poorly," Devel. 124:4121-4131 (1997).
Maione, B., et. al. "Activation of Endogenous Nucleases in Mature Sperm Cells upon Interaction with Exogenous DNA," DNA and Cell Biology 16:1087-1097 (1997).
Maione, B., et. al., "Sperm-Mediated Gene Transfer in Mice," Mol. Rep. & Devel. 50:406-409 (1998).
Marijt, E., et al., "Multiple Minor Histocompatibility Antigen Disparities Between a Recipient and Four HLA-Identical Potential Sibling Donors for Bone Marrow Transplantation," Human Immunology 37:221-228 (1993).

McKenzie, J., "Life-Saving Embryo?" http://www.abcnews.go.com/onair/WorldNewsTonight/wnt001003_testubebaby_feature.ht, Oct. 25, 2000, pp. 1-2.

Medin, J. A., et al., Gene Therapy of Enzyme and Immune Deficiencies in the Hemopoietic System, pp. 386-413.

Miller, D. J., et al., "Complementarity Between Sperm Surface β-1,4-Galactosyl-Transferase and Egg-Coat ZP3 Mediates Sperm-Egg Binding," Nature 357:589-593 (1992).

Morawatz, R., Written Opinion, issued on Jun. 27, 2002 by PTO regarding International Application No. PCT/US01/07018, which claims the priority to U.S. Appl. No. 09/537,861, 9 pages.

Mori, K., et al., "Blocking of Human Fertilization by Carbohydrates," Human Reproduction 8:1729-1732 (1993).

Nakamura, et al., "Identification and Characterization of a Sperm Peptide Antigen Recognized by a Monoclonal Antisperm Autoantibody Derived from a Vasectomized Mouse," Biochem. & Biophys. Res. Communications 205:1503-1509 (1994).

Naz, et al., "Antibodies to Sperm-Specific Human FA-1 Inhibit in Vitro Fertilization in Rhesus Monkeys: Development of a Simian Model for Testing of anti-FA-1 Contraceptive Vaccine," Journal of Reproductive Immunology 27:111-121 (1994).

Neural Differentiation of Rhesus Embryonic Stem Cells, http://www.ncbi.nlm.nih.gov/entrez/guery.fcgi?cmd-Retrieve&db-PubMed&list_uids-95.2. Oct. 25, 2000, p. 1.

Nikkhah, G., et al., "Microtransplantation of Nigral Dopamine Neurons a Step-by-Step Recipe," Neuromethods 36:207-231.

NT2PrecursorCells, Instruction Manual, Catalog #204101, Revision #079006 (1999).

Pain, B., et al., "Chicken Embryonic Stem Cells and Transgenic Strategies," Cells Tissues Organs 165:212-219 (1999).

Palacios, R., et al., "In Vitro Generation of Hematopoietic Stem Cells From an Embryonic Stem Cell Line," Proc. Natl. Acad. Sci. USA 92:7530-7534 (1995).

Pechan, P. A., et al., "Gene Therapy for Ischemic Stroke," Gene Therapy for Neurological Disorders and Brain Tumors, pp. 397-408.

Pereira, B., et al., "Rat Sperm Surface Mannosidase Is First Expressed on the Plasma Membrane of Testicular Germ Cells," Biology of Reproduction 59:1288-1295 (1998).

Perry, A. C. et al., "Mammalian Transgenesis by intracytoplasmic sperm injection," Science 284:1180-1183 (1999).

Pursel, V. G., et.al., "Genetic Engineering of Livestock," Science 244:1281-1288 (1989).

Qu, Z., et al., "Development of Approaches to Improve Cell Survival in Myoblast Transfer Therapy," The Journal of Cell Biology 142:1257-1267 (1998).

Reubinoff, B. E., et al., "Embryonic Stem Cell Lines from Human Blastocysts: Somatic Differentiation In Vitro," Nature Biotechnology, vol. 18, Apr. 2000.

Richardson, R. T., et al., "Sequence of a Rabbit Sperm Zona Pellucida Binding Protein and Localization during the Acrosome Reaction," Developmental Biology 165:688-701 (1994).

Rivkin, E., et al., "Molecular Cloning of Rat Sperm Galactosyl Receptor, a C-Type Lectin With In Vitro Egg Binding Activity," Molecular Reproduction and Development 56:401-411 (2000).

Rohwedel, J., et al., "Muscle Cell Differentiation of Embryonic Stem Cells Reflects Myogenesis in Vivo: Developmentally Regulated Expression of Myogenic Determination Genes and Functional Expression of Ionic Currents," Developmental Biology 164:87-101 (1994).

Rottmann, O. J., et. al., "Liposome Mediated Gene-Transfer via Sperm Cells. High Transfer Efficiency and Persistence of Transgenes by Use of Liposomes and Sperm Cells and a Murine Amplification Element," J. Animal Breed. Genet. 113:401-411 (1996).

Sarkar, et al., "Distribution of 105kDa Sperm Unique Antigen on Goat Epididymal Mature Spermatozoa," Biochem. & Biophys. ReS. Comm. 231:662-666 (1997).

Schuldiner, M., et al., "Effects of Eight Growth Factors on the Differentiation of Cells Derived from Human Embryonic Stem Cells," PNAS 97:11307-11312 (2000).

Senut, M. C., et al., "Gene Transfer for Adult CNS Regeneration and Aging," Gene Therapy for Neurological Disorders and Brain Tumors, pp. 345-375.

Shala, C., et al., "Monoclonal Antibody Against a Human Sperm Protein Recognizes Multiple Epitopes on Rabbit and Human Sperm and Blocks Sperm Function," Hybridoma 12:709-718 (1993).

Shamila, Y., et al., "Sperm-Mediated Gene Transfer in the Silkworm Bonyx Mori," Arch. Insect Biochem. Physiol. 37:168-177 (1998).

Slager, H. G., et al., "Transforming Growth Factor-β in the Early Mouse Embryo: Implications for the Regulation of Muscle Formation and Implantation," Developmental Genetics 14:212-224 (1993).

Smith, K., "Sperm Cell Mediated Transgenesis: A Review," Animal Biotech. 10:1-13 (1999).

Spadafora, C., "Sperm Cells and Foreign DNA: a Controversial Relation," BioEssays 20:955-964 (1998).

Sperandio, S., et. al., "Sperm Mediated DNA Transfer in Bovine and Swine Species," Animal Biotechnology 7:59-77 (1996).

Squires, E.J., "Status of Sperm-mediated Delivery Methods for Gene Transfer," Transgenic Animals in Agriculture, pp. 87-95 (1999).

Thomson, J. A., et al., "Embryonic Stem Cell Lines Derived from Human Blastocysts," Science 282:1145-1147 (1998).

Töpfer-Petersen, E., et al., "Sperm-Associated Protein Candidates for Primary Zona Pellucida-Binding Molecules: Structure-Function Correlations of Boar Spermadhesins," Journal of Reproduction and Fertility Supplement 50:55-61 (1996).

Töpfer-Petersen, E., et al., "Spermadhesins: A New Protein Family. Facts, Hypotheses and Perspectives," Andrologia 30:217-224 (1998).

Tsai, H. J., et. al., "Sperm as a Carrier to Introduce an Exogenous DNA Fragment into the Oocyte of Japanese Abalone (Haliotis Divorsicolor Suportexta)," Transgenic Research 6:85-95 (1997).

Uherek, C., et al., "DNA-Carrier Proteins for Targeted Gene Delivery," Advanced Drug Delivery Reviews 44:153-166 (2000).

Van Hennik, P. B., et al., "Highly Efficient Transduction of the Green Fluorescent Protein Gene in Human Umbilical Cord Blood Stem Cells Capable of Cobblestone Formation in Long-Term Cultures and Multilineage Engraftment of Immunodeficient Mice," Blood 92:4013-4022 (1998).

Varga, C. M., et al., "Receptor-Mediated Targeting of Gene Delivery Vectors: Insights from Molecular Mechanisms for Improved Vehicle Design," Biotechnology and Bioengineering 70:593-605 (2000).

Wall, R. J., et. al., "Making Transgenic Livestock, Genetic Engineering on a Large Scale," J. Cell. Biochem. 49:113-120 (1992).

Wallen-Ohman, M., et al., "Ligation of MHC Class I Induces Apoptosis in Human Pre-B Cell Lines, In Promyelocytic Cell Lines and in CD40-Stimulated Mature B Cells," International Immunology 9:599-606.

Ward, K., "The Application of Transgenic Techniques for the Improvement of Domestic Animal Productivity," Current Opinion in Biotechnology 2:834-839 (1991).

Weissman, I. L., et al., "Translating Stem and Progenitor Cell Biology to the Clinic: Barriers and Opportunities," Science 287:1442-1446 (2000).

What is HLA, http://www.innogenetics.com/Website/Website.nsf/7df3b6bb9c0862e8c12567380052687f/e, Oct. 24, 2000, pp. 1-6.

Wiles, M. V., et al., "Multiple Hematopoietic Lineages Develop from Embryonic Stem (ES) Cells in Culture," Development III, 259-267 (1991).

Wolf, et al., "Special Review Series—Gene Manipulation and Integrative Physiology," Experimental Physiology 85:615-625 (2000).

Wolf, E., et al., "Transgenic Technology in Farm Animals—Progress and Perspectives," The Experimental Physiology, pp. 615-625 (2000).

Xu, M. J., et al., "Stimulation of Mouse and Human Primitive Hematopoiesis by Murine Embryonic Aorta-Gonad-Mesonephros-Derived Stromal Cell Lines," Blood 92:2032-2040 (1998).

Yamasaki, N., et al., "Expression of the Rabbit Sperm Protein Sp17 in Cos Cells and Interaction of Recombinant Sp17 With the Rabbit Zona Pellucida," Molecular Reproduction and Development 40:48-55 (1995).

Yan, Y. C., et al., "Characterization of cDNA Encoding a Human Sperm Membrane Protein Related to A4 Amyloid Protein," Proc. Natl. Acad. Sci. 87:2405-2408 (1990).

Yan, et al., "Characterization of Sperm Agglutinating Monoclonal Antibody and Purification of the Human Sperm Antigen," Int. J. Fertil. 31:77-85 (1986).

Yoder, M. C., et al., "In Vivo Repopulating Hematopoietic Stem Cells are Present in the Murine Yolk Sac at day 9.0 Postcoitus," Proc. Natl. Acad. Sci USA 94:6776-6780 (1997).

Zani, M., "The Mechanism of Binding of Exogenous DNA to Sperm Cells: Factors Controlling the DNA Uptake," Experimental Cell Research 217:57-64 (1995).

Zhu, X., et al., "Fertilization Antigen-1: cDNA Cloning, Testis-Specific Expression, and Immunocontraceptive Effects," Proc. Natl. Acad. Sci. 94:4704-4709 (1997).

Chiu, W.W.C., et al., "Use of Antisperm Antibodies in Differential Display Western Blotting to Identify Sperm Proteins Important in Fertility," Human Reproduction 17(4):984-989 (2002).

Gleicher, N., et al. "How Does the Immune System Affect IVF?" First World Conference: International Association of Private Assisted Reproductive Technology Clinics and Laboratories, Venice, Italy, Mar. 13-18, 1999; abstract in Journal of Assisted Reproduction and Genetics vol. 16, No. 3, p. 144.

Pagidas, K., et al., "The Effect of Antisperm Autoantibodies in Male or Female Partners Undergoing In Vitro Fertilization-Embryo Transfer," Fertil. Steril. 62(2):363-369 (1994).

\* cited by examiner

Figure 2    Flow Cytometry Analyses for mAb C Binding to Sperm Cells in Different Species lane 1: *Sal I* cut pCMV-β plasmid
lane 2: *Sal I* cut pCMV-β plasmid in Modified Tyrode's medium
lane 3: *Sal I* cut pCMV-β plasmid + 0.2 µl mAb C
lane 4: *Sal I* cut pCMV-β plasmid + 1.0 µl mAb C
lane 5: *Sal I* cut pCMV-β plasmid + 2.5 µl mAb C
lane 6: *Sal I* cut pCMV-β plasmid + 6.0 µl mAb C
lane 7: *Sal I* cut pCMV-β plasmid + 10.0 µl mAb C
lane 8: *Sal I* cut pCMV-β plasmid in Modified Tyrode's medium pSEAP2-Control Vector Information
GenBank Accession #: U89938
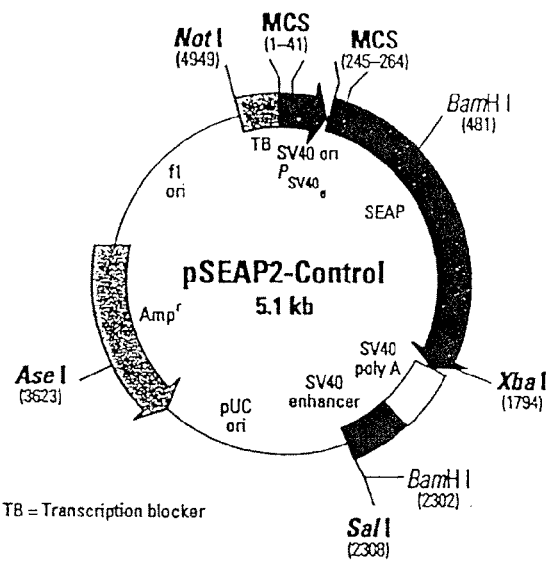
Restriction Map and Multiple Cloning Site (MCS) of pSEAP2-Control. Unique restriction sites are in bold.
FIGURE 7

```
  1 ATGACCAACA AGTGTCTCCT CCAAATTGCT CTCCTGTTGT GCTTCTCCAC TACAGCTCTT
 61 TCCATGAGCT ACAACTTGCT TGGATTCCTA CAAAGAAGCA GCAATTTTCA GTGTCAGAAG
121 CTCCTGTGGC AATTGAATGG GAGGCTTGAA TATTGCCTCA AGGACAGGAT GAACTTTGAC
181 ATCCCTGAGG AGATTAAGCA GCTGCAGCAG TTCCAGAAGG AGGACGCCGC ATTGACCATC
241 TATGAGATGC TCCAGAACAT CTTTGCTATT TTCAGACAAG ATTCATCTAG CACTGGCTGG
301 AATGAGACTA TTGTTGAGAA CCTCCTGGCT AATGTCTATC ATCAGATAAA CCATCTGAAG
361 ACAGTCCTGG AAGAAAAACT GGAGAAAGAA GATTTCACCA GGGGAAAACT CATGAGCAGT
421 CTGCACCTGA AAAGATATTA TGGGAGGATT CTGCATTACC TGAAGGCCAA GGAGTACAGT
481 CACTGTGCCT GGACCATAGT CAGAGTGGAA ATCCTAAGGA ACTTTTACTT CATTAACAGA
541 CTTACAGGTT ACCTCCGAAA CTGA
```

Human Interferon Beta

FIGURE 16

SEQUENCE LISTING

```
<160> NUMBER OF SEQ ID NOS: 4

<210> SEQ ID NO 1
<211> LENGTH: 5255
<212> TYPE: DNA
<213> ORGANISM: Gallus gallus

<400> SEQUENCE: 1
ggtaccgagc tcttacgcgt gctagcccgg gctcgagatc tgcgatctgc atctcaatta      60
gtcagcaacc atagtcccgc ccctaactcc gcccatcccg cccctaactc cgcccagttc     120
cgcccattct ccgccccatc gctgactaat ttttttttatt tatgcagagg ccgaggccgc     180
ctcggcctct gagctattcc agaagtagtg aggaggcttt tttggaggcc taggcttttg     240
caaaaagctt ggcattccgg tactgttggt aaagccacca tggaagacgc caaaaacata     300
aagaaaggcc cggcgccatt ctatccgctg gaagatggaa ccgctggaga gcaactgcat     360
```

```
aaggctatga agagatacgc cctggttcct ggaacaattg cttttacaga tgcacatatc    420
gaggtggaca tcacttacgc tgagtacttc gaaatgtccg ttcggttggc agaagctatg    480
aaacgatatg ggctgaatac aaatcacaga atcgtcgtat gcagtgaaaa ctctcttcaa    540
ttctttatgc cggtgtttgggcgcgttattt atcggagttg cagttgcgcc cgcgaacgac    600
atttataatg aacgtgaatt gctcaacagt atgggcattt cgcagcctac cgtggtgttc    660
gtttccaaaa aggggttgca aaaattttg aacgtgcaaa aaagctccc aatcatccaa      720 aaaattatta tcatggattc taaaacggat taccagggat ttcagtcgat gtacacgttc    780
gtcacatctc atctacctcc cggttttaat gaatacgatt tgtgccaga gtccttcgat     840 agggacaaga caattgcact gatcatgaac tcctctggat ctactggtct gcctaaaggt    900
gtcgctctgc ctcatagaac tgcctgcgtg agattctcgc atgccagaga tcctattttt    960
ggcaatcaaa tcattccgga tactgcgatt ttaagtgttg ttccattcca tcacggtttt    1020
ggaatgttta ctacactcgg atatttgata tgtggatttc gagtcgtctt aatgtataga    1080
tttgaagaag agctgtttct gaggagcctt caggattaca agattcaaag tgcgctgctg    1140
gtgccaaccc tattctcctt cttcgccaaa agcactctga ttgacaaata cgatttatct    1200
aatttacacg aaattgcttc tggtggcgct cccctctcta aggaagtcgg ggaagcggtt    1260
gccaagaggt tccatctgcc aggtatcagg caaggatatg gctcactga gactacatca     1320 gctattctga ttacacccga gggggatgat aaaccgggcg cggtcggtaa agttgttcca    1380 tttttttgaag cgaaggttgt ggatctggat accgggaaaa cgctgggcgt taatcaaaga    1440
ggcgaactgt gtgtgagagg tcctatgatt atgtccggtt atgtaaacaa tccggaagcg    1500
accaacgcct tgattgacaa ggatggatgg ctacattctg agacatagc ttactgggac     1560 gaagacgaac acttcttcat cgttgaccgc ctgaagtctc tgattaagta caaaggctat    1620
caggtggctc ccgctgaatt ggaatccatc ttgctccaac accccaacat cttcgacgca    1680
ggtgtcgcag gtcttcccga cgatgacgcc ggtgaacttc ccgccgccgt tgttgttttg    1740
gagcacggaa agacgatgac ggaaaaagag atcgtggatt acgtcgccag tcaagtaaca    1800
accgcgaaaa agttgcgcgg aggagttgtg tttgtggacg aagtaccgaa aggtcttacc    1860
ggaaaactcg acgcaagaaa aatcagagag atcctcataa aggccaagaa gggcggaaag    1920
atcgccgtgt aattctagag tcggggcggc cggccgcttc gagcagacat gataagatac    1980
attgatgagt ttggacaaac cacaactaga atgcagtgaa aaaaatgctt tatttgtgaa    2040
atttgtgatg ctattgcttt atttgtaacc attataagct gcaataaaca agttaacaac    2100
aacaattgca ttcattttat gtttcaggtt caggggggagg tgtgggaggt ttttttaaagc    2160 aagtaaaacc tctacaaatg tggtaaaatc gataaggatc tgaacgatgg agcggagaat    2220
gggcggaact gggcggagtt aggggcggga tgggcggagt taggggcggg actatggttg    2280
ctgactaatt gagatgcatg cttttgcatac ttctgcctgc tggggagcct ggggactttc    2340
cacacctggt tgctgactaa ttgagatgca tgctttgcat acttctgcct gctggggagc    2400
ctggggactt ccacacccct aactgacaca cattccacag cggatccgtc gaccgatgcc    2460
cttgagagcc ttcaacccag tcagctcctt ccggtgggcg cggggcatga ctatcgtcgc    2520
cgcacttatg actgtcttct ttatcatgca actcgtagga caggtgccgg cagcgctctt    2580
ccgcttcctc gctcactgac tcgctgcgct cggtcgttcg gctgcggcga gcggtatcag    2640
ctcactcaaa ggcggtaata cggttatcca cagaatcagg ggataacgca ggaaagaaca    2700
tgtgagcaaa aggccagcaa aaggccagga accgtaaaaa ggccgcgttg ctggcgtttt    2760
```

```
tccataggct ccgcccccct gacgagcatc acaaaaatcg acgctcaagt cagaggtggc   2820
gaaacccgac aggactataa agataccagg cgtttccccc tggaagctcc ctcgtgcgct   2880
ctcctgttcc gaccctgccg cttaccggat acctgtccgc ctttctccct cgggaagcg    2940 tggcgctttc tcatagctca cgctgtaggt atctcagttc ggtgtaggtc gttcgctcca   3000
agctgggctg tgtgcacgaa ccccccgttc agcccgaccg ctgcgcctta ccggtaact    3060 atcgtcttga gtccaacccg gtaagacacg acttatcgcc actggcagca gccactggta   3120
acaggattag cagagcgagg tatgtaggcg gtgctacaga gttcttgaag tggtggccta   3180
actacggcta cactagaaga acagtatttg gtatctgcgc tctgctgaag ccagttacct   3240
tcggaaaaag agttggtagc tcttgatccg gcaaacaaac caccgctggt agcggtggtt   3300 ttttgtttg caagcagcag attacgcgca gaaaaaaagg atctcaagaa gatcctttga     3360
tcttttctac ggggtctgac gctcagtgga acgaaaactc acgttaaggg attttggtca   3420
tgagattatc aaaaggatc ttcacctaga tccttttaaa ttaaaaatga gttttaaat      3480 caatctaaag tatatatgag taaacttggt ctgacagtta ccaatgctta atcagtgagg   3540
cacctatctc agcgatctgt ctatttcgtt catccatagt tgcctgactc cccgtcgtgt   3600
agataactac gatacgggag ggcttaccat ctggccccag tgctgcaatg ataccgcgag   3660
acccacgctc accggctcca gatttatcag caataaacca gccagccgga agggccgagc   3720
gcagaagtgg tcctgcaact ttatccgcct ccatccagtc tattaattgt tgccgggaag   3780
ctagagtaag tagttcgcca gttaatagtt tgcgcaacgt tgttgccatt gctacaggca   3840
tcgtggtgtc acgctcgtcg tttggtatgg cttcattcag ctccggttcc caacgatcaa   3900
ggcgagttac atgatccccc atgttgtgca aaaaagcggt tagctccttc ggtcctccga   3960
tcgttgtcag aagtaagttg gccgcagtgt tatcactcat ggttatggca gcactgcata   4020
attctcttac tgtcatgcca tccgtaagat gcttttctgt gactggtgag tactcaacca   4080
agtcattctg agaatagtgt atgcggcgac cgagttgctc ttgcccggcg tcaatacggg   4140
ataataccgc gccacatagc agaactttaa aagtgctcat cattggaaaa cgttcttcgg   4200
ggcgaaaact ctcaaggatc ttaccgctgt tgagatccag ttcgatgtaa cccactcgtg   4260
cacccaactg atcttcagca tcttttactt tcaccagcgt ttctgggtga gcaaaaacag   4320
gaaggcaaaa tgccgcaaaa aagggaataa gggcgacacg gaaatgttga atactcatac   4380
tcttcctttt tcaatattat tgaagcattt atcaggggtta tgtctcatg agcggataca    4440 tatttgaatg tatttagaaa aataaacaaa taggggttcc gcgcacattt ccccgaaaag   4500
tgccacctga cgcgccctgt agcggcgcat taagcgcggc gggtgtggtg gttacgcgca   4560
gcgtgaccgc tacacttgcc agcgccctag cgcccgctcc tttcgctttc ttcccttcct   4620
ttctcgccac gttcgccggc tttccccgtc aagctctaaa tcggggggctc ccttagggt    4680 tccgatttag tgctttacgg cacctcgacc ccaaaaaact tgattagggt gatggttcac   4740
gtagtgggcc tcgccctgat agacggtttt tcgccctttg acgttggagt ccacgttctt   4800
taatagtgga ctcttgttcc aaactggaac aacactcaac cctatctcgg tctattctttt  4860 tgatttataa gggattttgc cgatttcggc ctattggtta aaaaatgagc tgatttaaca   4920
aaaatttaac gcgaatttta acaaaatatt aacgcttaca atttgccatt cgccattcag   4980
gctgcgcaac tgttgggaag ggcgatcggt gcgggcctct tcgctattac gccagcccaa   5040
gctaccatga taagtaagta atattaaggt acggggagta cttggagcgg ccgcaataaa   5100
atatctttat tttcattaca tctgtgtgtt ggttttttgt gtgaatcgat agtactaaca   5160
```

-continued

```
tacgctctcc atcaaaacaa aacgaaacaa aacaaactag caaaataggc tgtccccagt    5220
gcaagtgcag gtgccagaac atttctctat cgata                                5255

<210> SEQ ID NO 2
<211> LENGTH: 20
<212> TYPE: DNA
<213> ORGANISM: Artificial
<220> FEATURE:
<223> OTHER INFORMATION: upper primer

<400> SEQUENCE: 2
ttacagatgc acatatcgag                                                   20

<210> SEQ ID NO 3
<211> LENGTH: 20
<212> TYPE: DNA
<213> ORGANISM: Artificial
<220> FEATURE:
<223> OTHER INFORMATION: lower primer

<400> SEQUENCE: 3
catactgttg agcaattcac                                                   20

<210> SEQ ID NO 4
<211> LENGTH: 564
<212> TYPE: DNA
<213> ORGANISM: Homo sapiens

<400> SEQUENCE: 4
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tattgcctca aggacaggat gaactttgac     180
atccctgagg agattaagca gctgcagcag ttccagaagg aggacgccgc attgaccatc     240
tatgagatgc tccagaacat ctttgctatt ttcagacaag attcatctag cactggctgg     300
aatgagacta ttgttgagaa cctcctggct aatgtctatc atcagataaa ccatctgaag     360
acagtcctgg aagaaaaact ggagaaagaa gatttcacca ggggaaaact catgagcagt     420
ctgcacctga aaagatatta tgggaggatt ctgcattacc tgaaggccaa ggagtacagt     480
cactgtgcct ggaccatagt cagagtggaa atcctaagga actttactt cattaacaga     540 cttacaggtt acctccgaaa ctga                                            564
```

METHOD AND COMPOSITION FOR GENETICALLY MODIFYING NON-HUMAN CELLS AND ANIMALS

CROSS-REFERENCE TO RELATED APPLICATIONS

The present application is a continuation-in-part of U.S. patent application Ser. No. 11/407,851, now abandoned, filed Apr. 20, 2006 which was filed as a continuation of U.S. patent application Ser. No. 09/537,861, now U.S. Pat. No. 7,067,308, filed Mar. 28, 2000, and U.S. patent application Ser. No. 11/372,241, now abandoned, filed Mar. 9, 2006 which was filed as a continuation of U.S. patent application Ser. No. 09/781,046 now U.S. Pat. No. 7,053,187, filed on Feb. 8, 2001, which was filed as a continuation-in-part application of U.S. patent application Ser. No. 09/537,861, now U.S. Pat. No. 7,067,308, filed on Mar. 28, 2000, the disclosures of all of which are incorporated herein by reference as if fully set forth herein, including drawings.

FIELD OF INVENTION

The present invention relates to the field of genetic modification of oocytes, cells and in non-human animals. The invention also relates to vector systems for gene and stem cell therapy and methods and systems for introducing a gene into a cell.

BACKGROUND OF THE INVENTION

Efficient genetic modification of animals, especially in higher mammals, has been a major goal of researchers in the biotechnology field for the last two decades. Not only can genetic modification of animals advance our understanding of genes and gene-functions in multi-cell organisms, it can also serve useful applications in the bio-agricultural industry as well as bio-drug industry. Examples of these applications include raising livestock with desired characteristics such as faster growth rate, production of therapeutic proteins in milk, or even the generation of more "humanized" organs from animals for use in animal to human xenotransplantation. Genetic modification of animals with human genes are also valuable as pharmaceutical bioreactors. Human proteins expressed in transgenic animals such as chicken also provide a better economic alternative to bacteria or yeast expression systems due to their reduced production costs.

In theory, transgenic chickens should be ideal bioreactors for making large quantities of recombinant proteins. However, due to the large size of avian eggs and the difficulty in harvesting an egg before it has begun developing into a chick has greatly hindered progress in this field. The most common way to make a transgenic animal is to harvest a newly fertilized oocyte and inject foreign DNA directly into nucleus using microinjection technology. While this task has become fairly routine in mammalian transgenics, it is not the case with avian transgenics. Not only are chicken zygotes difficult to harvest from the chicken's oviduct, but once harvested, the single cell is difficult to locate within the viscous yellow yolk.

Current techniques to modify the genome include microinjection of foreign DNA into the pronuclei of fertilized eggs, delivery of foreign DNA into embryonic stem cells in vitro or blastomere cells in vivo through lipid-based agents, electroporation, or viral infection. Aside from mice, however, genetic modification techniques have had limited success in other animals. The microinjection technique, for example, has been reported to be technically very demanding and requires the use of highly sensitive and expensive equipment. The viability of embryos after microinjection has also been reported to be very poor. Wall, R. J., et. al. (1992) Making Transgenic Livestock, Genetic Engineering on a Large Scale, *Journal of Cellular Biochemistry*, Vol. 49, pp. 113-120. This has led researchers in the field to investigate alternative and easier ways of delivering genes into an animal.

In 1989, Lavitrano, M., et. al. reported that simply incubating foreign DNA with mice's sperm cells and effecting fertilization in vitro could lead to genetically modified mice. Lavitrano, M., et. al. (1989) Sperm Cells as Vectors for Introducing Foreign DNA into Eggs—Genetic Transformation of Mice, *Cell*, Vol. 57, pp. 717-723. Characterized as the "cold fusion" equivalent in biotechnology, this report generated much excitement in the field. Birnstiel, M., et. al. (1989) Dangerous Liaisons: Spermatozoa as Natural Vectors for Foreign DNA?, *Cell*, Vol. 57, pp. 701-702. Those skilled in the art, however, are reported to remain skeptical even to this day about the Lavitrano's report since a number of researchers in the field have reportedly failed to repeat the experiment. Brinster, R., et. al. (1989) No Simple Solution for Making Transgenic Mice, *Cell*, Vol. 59, pp. 239-241; Smith, K. (1999) Sperm Cell Mediated Transgenesis: A Review, *Animal Biotechnology*, Vol. 10(1&2), pp. 1-13.

Over the last decade, efforts have continued to explore the use of sperm cells as a vector for mediating gene transfer in animals. Researchers have elucidated that sperm cells have the inherent ability to internalize foreign DNA. Francolini, M., et. al (1993) Evidence for Nuclear Internalization of Exogenous DNA into Mammalian Sperm Cells, *Mol. Reprod. Devel.*, Vol. 34, pp. 133-139. Yet, certain inhibitory factors present in seminal fluid may inhibit this ability to take up DNA. Lavitrano, M., et. al. (1992) The Interaction Between Exogenous DNA and Sperm Cells, *Mol. Reprod. Devel.*, Vol. 31, pp. 161-169. In addition, foreign DNA introduced into sperm cells may also suffer from extensive DNA rearrangement because in mature sperm cells, internalization of foreign DNA may activate certain endogenous nucleases in these cells. Maione, B. et. al. (1997) Activation of Endogenous Nucleases in Mature Sperm Cells upon Interaction with Exogenous DNA, *DNA and Cell Biology*, Vol. 16, pp. 1087-1097. Such rearrangement could threaten the usefulness of genetically modified animals using this technique.

Other work with sperm cells as vector have focused on the use of either lipid-based agents or electroporation to deliver foreign DNA into the sperm cells. Smith, supra; Rottman R., et. al. (1996) Liposome-mediated Gene Transfer via Sperm Cells. High Transfer Efficiency and Persistence of Transgenes by Use of Liposomes and Sperm Cells and a Murine Amplification Element, *Journal of Animal Breeding and Genetics*, Vol. 113, pp. 401-411; PCT Publications WO 99/42569, WO 99/40213, and WO 97/11597. Such methods may also suffer from the same problem of DNA internalization and exposure to nucleases that could cause rearrangement of the foreign DNA being introduced. In addition, lipid-based agents, which are often toxic, and electroporation may require extensive experimentation to prevent the death or the loss of sperm cell motility. Other techniques have also focused on using recombinant virus infection, as disclosed in PCT Publications WO 99/38991, or on using a "gene gun" with micro-carriers, as disclosed in PCT Publication WO 93/24626, to introduce foreign DNA into sperm cells. Such techniques may be technically challenging and may also affect the viability and motility of the sperm cells. They may also suffer from the same problem of DNA internalization and exposure to nucleases that could cause rearrangement of the foreign DNA being introduced.

Since 1989, researchers have reported the use of sperm cells as vectors in different animals ranging from insects, marine animals, amphibians, birds, and mammals. Smith, supra. However, few reported that the genetic modification was observed in viable mature offspring. Smith, supra. More problematic is the fact that some reports used only PCR analysis to verify the existence of the foreign DNA in the cells. These reports are summarized in table one of Gandolfi, F. (1998) Spermatozoa, DNA Binding and Transgenic Animals, *Transgenic Research*, Vol. 7, pp. 147-155. Since PCR cannot distinguish between foreign DNA transmitted through episomes or through the chromosomal DNA, Gandolfi has questioned the value of these reports stating that it "opens up an important argument relating to appropriate evaluation of the results described in some reports." Gandolfi, supra. Episomal transmission is not as desirable as chromosomal transmission since the episome may be lost during subsequent cell division, and the desired effect of genetic modification may never be expressed in adult animals.

Because an easy, non-toxic, and efficient way of genetically modifying animals, especially in the field of transgenic chicken systems, can greatly advance transgenic technology, a new way of using sperm cells for delivering genes into animals is needed. The present invention provides these advantages among other benefits. Rather than manipulate a host oocycte by microinjection, the present invention incorporates use of agents which link exogenous DNA to a sperm cell, allowing entry of the foreign DNA into a host cell. Also included are systems for expressing therapeutic proteins in the transgenic embryos or animals created by the present methods.

SUMMARY OF THE INVENTION

The present invention is directed to a vector and its use to generate genetically modified cells, embryos and animals. One aspect of this invention involves a vector that comprises a sperm cell and one or more polynucleotide molecules bound to a sperm cell through one or more non-liposome based linkers. The sperm cell can be any animal sperm cell, preferably a non-human animal. A desirable sperm cell includes an avian sperm cell. In one embodiment of the invention, the one or more polynucleotide molecules encode for a gene product that confers desired characteristics in the cells or the animals. In another embodiment, the polynucleotide encodes for a therapeutic protein. In another embodiment, the linker is a protein or polypeptide, preferably a sperm specific linker that binds with the external surface of the sperm cell. The linker interacts with one or more polynucleotide molecules such as by ionic interaction. The linker may be one or more antibody such as an anti-sperm antibody. This interaction can also be carried out by different molecular interactions, including the use of another or secondary linker. The association of the sperm, linker, and the one or more polynucleotide can also occur in vitro or in vivo.

In another aspect of the present invention, genetically modified cells or animals are derived from the fertilization of an animal egg cell with the vector described above. Fertilization can occur in vitro or in vivo. In one embodiment, genetic modification occurs with the polynucleotide molecule integrating, wholly or partially, into the cell or animal's genome. Another aspect of the present invention includes cells, such as sperm cells or egg cells, cell lines, embryos and offspring that are derived from these genetically modified animals or their descendants.

In another aspect of the present invention, the genetically modified embryos are transgenic eggs which are useful as protein expression systems. Such transgenic embryos are valuable as pharmaceutical bioreactors which are ideal for making large quantities of recombinant proteins.

In another aspect of the present invention, the genetically modified animals derived from the use of the sperm vector described above possess certain desired characteristics. Examples of these characteristics include faster growth rates, disease or pathogen resistance, high production of certain proteins, and organs suitable for animal to human xenotransplantation.

BRIEF DESCRIPTION OF THE DRAWINGS

FIG. 7 shows the plasmid map of pSEAP-2-control. pSEAP2-control is a positive control vector expressing secreted alkaline phosphate (SEAP) under the control of the SV40 early promoter and the SV40 enhancer. The SEAP coding sequence is followed by the SV40 late polyadenylation signal to ensure proper, efficient processing of the SEAP transcript in eukaryotic cells. A synthetic transcription blocker (TB) composed of adjacent polyadenylation and transcription pause sites and located upstream of the multiple cloning site (MCS) reduces background transcription. The vector backbone also contains an F1 origin for single-stranded DNA production, a pUC origin of replication, and an ampicillin resistance gene for propagation and selection in *E. coli* The SEAP2 vectors incorporate a number of features that improve the sensitivity of SEAP by increasing the efficiency of SEAP expression and enhancing the utility of the vectors. These include 1) an improved Kozak consensus translation initiation site, 2) removal of the SV40 small-T intron, which can cause cryptic splicing and reduced expression in some genes and/or small cell types, 3) switching from the early to late polyadenylation signal of SV40, which typically causes a five-fold increase in mRNA levels, 4) an expanded MCS, 5) compact plasmid size, and 5) removal of extraneous sequences from the 3'-untranslated region of the SEAP mRNA.

FIG. 16 shows the DNA sequence of human interferon-β [SEQ ID NO: 4].

GENERAL DESCRIPTION OF THE INVENTION

Figure 1:
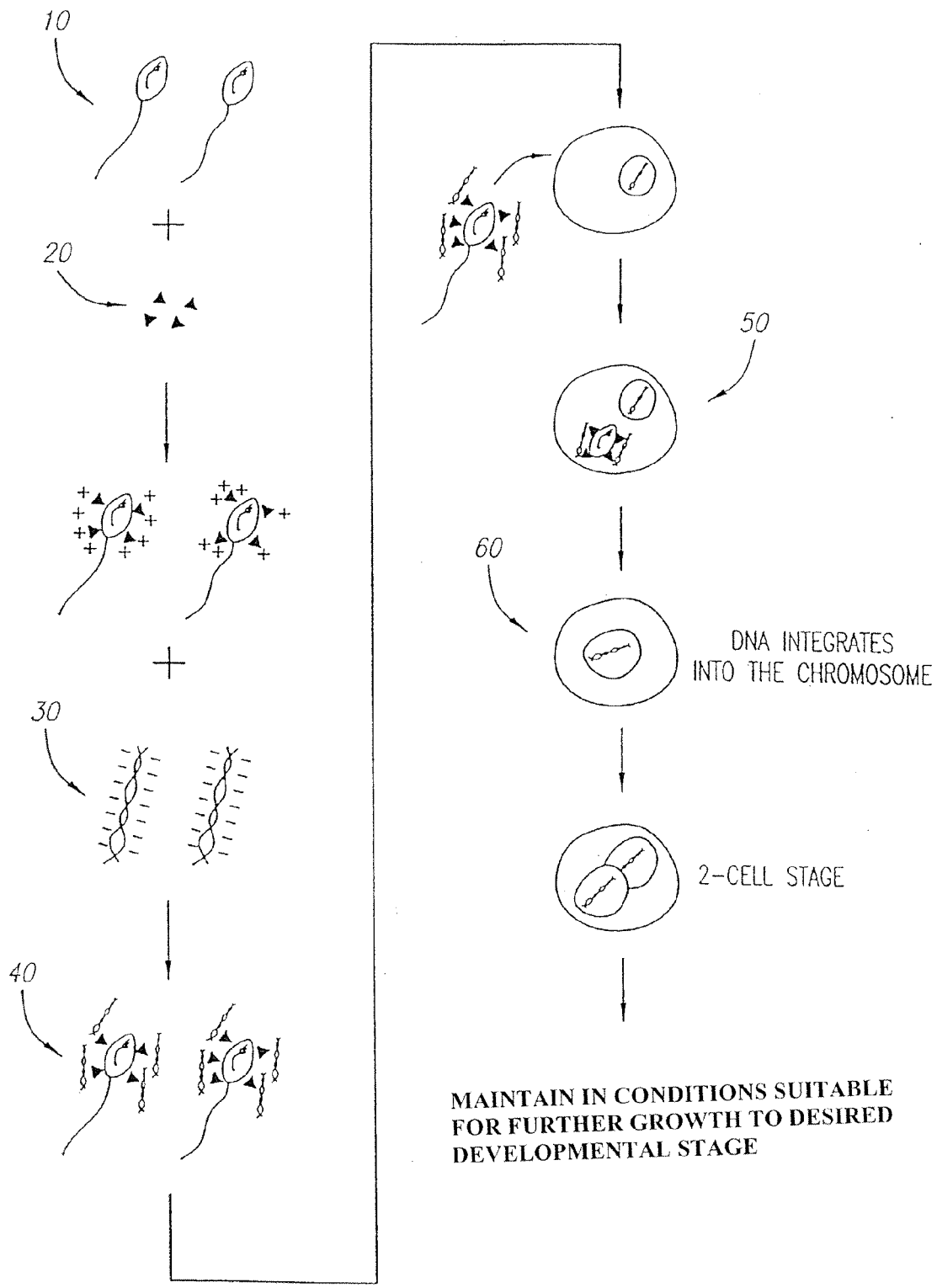
FIG. 1 is a pictorial representation of the basic steps involved in using one embodiment of the present invention.

All publications, patent applications, patents and other references mentioned herein are incorporated by reference in their entirety.

As used herein, the term "egg" means an oocyte surrounded by a zona pellucida and a mass of cumulus cells (follicle cells) with their associated proteoglycan. The term "oocyte" refers to a female gamete cell and includes primary oocytes, secondary oocytes and mature, unfertilized ovum. An oocyte is a large cell having a large nucleus (i.e., the germinal vesicle) surrounded by ooplasm. The ooplasm contains non-nuclear cytoplasmic contents including mRNA, ribosomes, mitochondria and yolk proteins.

The term "sperm" refers to a male gamete cell and includes spermatogonia, primary spermatocytes, secondary spermatocytes, spermatids, differentiating spermatids, round spermatids, and spermatozoa.

The term "embryonic stem cell" or "stem cell" refers to a cell, which is an undifferentiated cell and may undergo terminal differentiation giving rise to many differentiated cell types in an embryo or adult, including the germ cells (sperm and eggs). This cell type is also referred to herein as an "ESC".

The term "animal" includes all invertebrate and vertebrate animals such as mammals (e.g., rodents, sheep, dogs, cows, pigs and primates, including monkeys, apes, and humans), amphibians, reptiles, fish and birds. It also includes an individual animal in all stages of development, including embryonic and fetal stages.

A "transgenic animal" or "genetically modified animal" refers to any animal, such as an avian (e.g. chicken, turkey, quail, and pheasant, etc.) or mammal (e.g., mouse, rat, squirrel, hamster, guinea pig, pig, baboons, squirrel monkey, and chimpanzee, etc.), or an amphibian, in which one or more cells contain exogenous nucleic acid introduced by way of human intervention. The transgene is introduced into the cell, directly or indirectly, by introduction into a precursor of the cell, by way of use of the methods described herein. In the transgenic animals described herein, the transgene can cause cells to express a structural gene of interest. Alternatively, the transgene can cause silencing of a structural gene of interest. However, transgenic animals in which a transgene is silent are also included. As used herein, the term "transgenic" is used interchangeably with "genetically modified".

When a bird is used as the animal into which a transgene is introduced, a desired or preselected protein can be obtained in the eggs derived from the transgenic bird in a productive and stable manner. Genes encoding proteins requiring a sugar chain(s) for activity are particularly suitable for such a expression system.

The term "transgenic embryo" refers to an embryo containing a transgene.

The term "transgenic cell" refers to a cell containing a transgene.

The term "exogenous nucleic acid," refers to nucleic acid that has been isolated or is in an isolated form. Exogenous nucleic acid includes those encoding for genes that are naturally present in the host cell, oocyte or sperm (eg. native or wild-type DNA sequences), as well as those encoding for genes that are not naturally present in the host cell, oocyte or sperm (e.g. foreign, non-native sequence). Also included are those nucleic acids which are present in a position other than its naturally occurring position in the host cell, oocyte or sperm. Exogenous nucleic acid includes those encoding for therapeutic proteins as well as proteins useful for diagnostic purposes. For example, the nucleic acid can encode a hormone, receptor, enzyme, or (poly) peptide of therapeutic value. Such methods can result in transient expression of non-integrated transferred DNA, extrachromosomal replication and expression of transferred replicons such as episomes, or integration of transferred genetic material into the genomic DNA of host cells.

The phrase "nucleic acid molecules" and the term "polynucleotide" denote polymeric forms of nucleotides of any length, either ribonucleotides or deoxynucleotides. They include single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of a polynucleotide can comprise sugars and phosphate groups, as is typical for RNA and DNA, or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. A polynucleotide may be further modified, such as by conjugation with a labeling component. Other types of modifications include caps, substitution of one or more of the naturally occurring nucleotides with an analog, and introduction of means for attaching the polynucleotide to proteins, metal ions, labeling components, other polynucleotides, or a solid support.

The term "gene" refers to a nucleic acid that comprises control and structural (e.g. coding) sequences necessary for the production of a ribonucleic acid and/or a polypeptide. The polypeptide can be encoded by a full length coding sequence or by any portion of the coding sequence so long as the desired function (or lack of function) is obtained.

Examples of suitable nucleic acids for use in the present invention include, but are not limited to, those nucleic acids encoding a gene for a hormone, growth factor, enzyme, cytokine, receptor, or MHC molecule having a therapeutic activity. Additionally, suitable genes for use in the compositions and methods of the present invention, include nucleic acid sequences that are exogenous or endogenous to cells into which the nucleic acid encoding the gene of interest can be introduced. Of particular interest and suitability for use in the compositions and methods of the present invention for treatment of disease are those genes encoding a polypeptide that is either absent, produced in diminished quantities, or produced in a mutant form in those subjects having or are susceptible to a genetic disease. Examples of such genetic diseases include, but are not limited to, retinoblastoma, Wilms tumor, adenosine deaminase deficiency (ADA), thalassemias, cystic fibrosis, Sickle cell disease, Huntington's disease, Duchenne's muscular dystrophy, Phenylketonuria, Lesch-Nyhan syndrome, Gaucher's disease, and Tay-Sach's disease.

Also of interest and suitable for use in the compositions and methods of the present invention for treatment of disease are nucleic acids encoding a tumor suppressor gene. Examples of such suitable tumor suppressor genes include, but are not limited to, retinoblastoma, GM-CSF, G-CSF, M-CSF, human growth hormone (HGH), TNF, TGF-.beta., TGF-.alpha., hemoglobin, interleukins, co-stimulatory factor B7, insulin, factor VIII, factor IX, PDGF, EGF, NGF, EPO, and .beta.-globin, as well as biologically or therapeutically active muteins of the proteins encoded by such genes. Suitable genes for delivery to target cells can be from any species, but preferably a mammalian or avian species. Further, preferred species, as sources of suitable genes, are those species into which the gene of interest is to be delivered using the methods and compositions of the present invention, e.g., a mammalian or avian species.

Further examples of suitable exogenous nucleic acids for use in the compositions and methods of the present invention include, but are not limited to, those that encode a protein or molecule having an antiinflammatory, antiviral, or anticancer activity. Examples of such suitable nucleic acids include, but are not limited to, those encoding a granulocyte macrophage stimulating colony factor (GMCSF) or variant thereof (e.g., Leukine™ or human GMCSFLeu.sup.23Asp.sup.27Glu.sup.39)), having an anticancer activity (see e.g., the GMCSF mutants of U.S. Pat. Nos. 5,032,676; 5,391,485; and 5,393,870). Also, for example, suitable exogenous nucleic acids include, but are not limited to, those encoding an interferon having an antiinflammatory or antiviral activity, e.g., an inteferon, particularly IFN-.beta., and more particularly, an IFN-.beta. 1α or IFN-.beta. 1β.

Human IFN-.beta. is a well-characterized polypeptide. The amino acid sequence of human IFN-.beta. is known (see e.g., Gene 10:11-15, 1980, and in EP 83069, EP 41313 and U.S. Pat. No. 4,686,191). Also, crystal structures have been reported for human and murine IFN-.beta., respectively (see e.g., Proc. Natl. Acad. Sci. USA 94:11813-11818, 1997. J. Mol. Biol. 253:187-207, 1995; reviewed in Cell Mol. Life. Sci. 54:1203-1206, 1998). In addition, protein-engineered variants of IFN-.beta. have been reported (see e.g., WO 9525170, WO 9848018, U.S. Pat. No. 5,545,723, U.S. Pat. No. 4,914,033, EP 260350, U.S. Pat. No. 4,588,585, U.S. Pat. No. 4,769,233, Stewart et al, DNA Vol. 6 No. 2 1987 pp. 119-128, Runkel et al, 1998, Jour. Biol. Chem. 273, No. 14, pp. 8003-8008). Also, the expression of IFN-.beta. in CHO cells has been reported (see e.g., U.S. Pat. No. 4,966,843, U.S. Pat. No. 5,376,567 and U.S. Pat. No. 5,795,779). Further, IFN-.beta. fusion proteins are reported, e.g., in WO 00/23472.

Additional suitable exogenous nucleic acids for use in the compositions and methods of the present invention, include those that encode a fusion or chimeric protein, or a fusion or chimeric nucleic acid (e.g., RNA). In some embodiments, an exogenous nucleic acid of the present invention can regulate expression of a gene product or block one or more steps in a biological pathway (e.g., a sepsis pathway) and, thereby, provide a therapeutic benefit. Standard methods for constructing nucleic acids encoding fusion or chimeric molecules are known in the art (see, e.g., Sambrook et al., Molecular Cloning: A Laboratory Manual, 2 nd ed., Cold Spring Harbor Laboratory, Cold Spring Harbor, N.Y. (1989); Ausubel et al. (eds.), Current Protocols In Molecular Biololgy, John Wiley and Sons (1987)).

The term "transgene" also broadly refers to any nucleic acid that is introduced into the genome of an animal or embryo, including but not limited to genes, fragments thereof (e.g., regulatory sequences or structural sequences) or DNA having sequences which are perhaps not normally present in the genome, genes which are present, but not normally transcribed and/or translated ("expressed") in a given genome, or any other gene or DNA which one desires to introduce into the genome. This may include genes which may normally be present in the non-transgenic genome but which one desires to have altered in expression, or which one desires to introduce in an altered or variant form. The transgene may also be foreign to the non-transgenic genome (e.g., reporter genes or DNA encoding hairpin siRNAs). The transgene may be specifically targeted to a defined genetic locus or may be randomly integrated within a chromosome. A transgene may therefore include one or more transcriptional regulatory sequences and any other nucleic acid, such as introns, that may be necessary for optimal expression of a selected nucleic acid. A transgene can be as few as a 100-150 bp of nucleotides long, but is preferably at about 2,000-30,000 nucleotides long and longer to more than 1 million nucleotides. A transgene can be coding or non-coding sequences, or a combination thereof. A transgene usually comprises a regulatory element that is capable of driving the expression of one or more nucleic acids under appropriate conditions.

The term "a structural gene" refers to a gene that expresses a biologically active protein of interest or a ribonucleic acid, such as an antisense RNA, ribozyme or siRNA. The term "structural gene" excludes the non-coding regulatory sequence which drives transcription. The structural gene may be derived in whole or in part from any source known to the art, including from a eukaryotic, prokaryotic, human, animal, plant, fungal, yeast, insect, viral or other source, or chemically synthesized. The structural gene may therefore also encode a fusion protein. A structural gene may contain one or more modifications in either the coding or the untranslated regions which could affect the biological activity or the chemical structure of the expression product, the rate of expression, or the manner of expression control. Such modifications include, but are not limited to, mutations, insertions, deletions, and substitutions of one or more nucleotides as is apparent to the skilled person. The structural gene may constitute an uninterrupted coding sequence or it may include one or more introns, bound by the appropriate splice junctions.

The term "gene expression" refers to the process by which a nucleotide sequence undergoes successful transcription and, for polypeptides, translation such that detectable levels of the delivered nucleotide sequence are expressed.

As used herein, the term "avian" is intended to include males and females of any avian species and is intended to encompass poultry which are commercially raised for eggs, meat or as pets. Accordingly, the term "avian" is particularly intended to encompass chickens, turkeys, ducks, geese, quail, pheasant, parakeets, parrots, cockatoo, cockatiel, ostrich, emu and the like. Alternatively, the avian is an endangered species of bird.

The terms "transgenic bird" and "transgenic embryo" are used herein in accordance with their generally understood meanings in the art. A transgenic bird or transgenic embryo contains an exogenous nucleic acid sequence or polynucleotide in one or more cells. The exogenous nucleic acid may originate from a different species (e.g., avian, mammalian, insect, bacterial, protozoan, yeast, fungal, viral) or from the same species. For example, an additional copy of a wild-type coding sequence or a mutated form of a coding sequence from the same species may be introduced. Alternatively, the exogenous polynucleotide may encode a protein useful for treatment or prevention of a disease. For example, the exogenous polynucleotide may encode for an antibody, antigen (e.g. for immunization), growth factor, hormone, enzyme, cytokine and the like. The exogenous nucleic acid may encode a polypeptide, an antisense RNA or other untranslated RNA. The exogenous nucleic acid is generally stably transformed into one or more cells in the transgenic bird or embryo, e.g., by stable integration into the genome or by introduction of an episomal construct that is stably maintained by the host cell. Those skilled in the art will appreciate that it is not necessary that every cell of the resulting transgenic bird or embryo contain the transgene. The exogenous nucleotide sequence may be DNA or RNA, and it may encode any polypeptide or peptide of interest or may encode a non-translated RNA (e.g. antisense RNAs or ribozymes).

In particular embodiments, the oocyte and host are from the same species. Alternatively, the oocyte may be from different strains or breeds of the same species (e.g. two different breeds or strains of chicken).

By "antibody" it is intended to include not only whole immunoglobulin molecules but also fragments thereof such as Fab, F(ab')2, Fv and other fragments thereof that retain the antigen-binding site. Similarly the term "antibody" includes genetically engineered derivatives of antibodies such as single chain Fv molecules (scFv) and domain antibodies (dAbs). The term also includes antibody-like molecules which may be produced using phage-display techniques or other random selection techniques for molecules which bind to MR or to specified regions of MR. Thus, the term antibody includes all molecules which contain a structure, preferably a peptide structure, which is part of the recognition site (i.e. the part of the antibody that binds or combines with the epitope or antigen) of a natural antibody.

Generally, FIG. 1 shows the basic steps involved in using one embodiment of the present invention to genetically modify cells or animals using a sperm vector. Briefly, animal sperm cells 10, are collected by methods known in the art or purchased commercially from sources such as Birchwood Genetics in West Manchester, Ohio, and are bound together with linkers 20. These linkers are preferably antibodies or immunoglobulins of the types, IgG, IgA or IgM, but they can also be other compounds such as peptides, glycoproteins, carbohydrates, or other chemical-compound linkers. These linkers bind or associate to the sperm cells' external surface through different molecular interactions such as ionic interaction, covalent bonds, Vander Waals forces, or ligand-receptor interaction. Circular or linear polynucleotide molecules 30 then bind or attach to the linkers on the sperm-linker complex—also through different molecular interactions such as ionic, covalent bonds, Vander Waals forces, or ligand-receptor interaction. These polynucleotide molecules may encode for certain gene products, but they may also be disrupted genes which are homologous with endogenous genes, which when introduced into the host egg cell, recombine into the egg chromosome to knockout a gene. The sperm-linker-DNA complex 40 formed can then be used to effectuate fertilization in vitro or in vivo. Upon fertilization, the polynucleotide is introduced into the fertilized egg 50 and embryo 60 and can integrate into the chromosome, becoming a part of a cell, embryo or animal's genetic material. It should be noted that, in some alternative embodiments of the present invention, the sequence of the steps of the flow chart of FIG. 1 may occur out of the order noted. For example, association of the sperm, linker and polynucleotide molecules which are noted as occurring in succession, may in fact be executed substantially concurrently or the association of the sperm, linker and polynucleotide molecules may sometimes be executed in the reverse (or otherwise different) order. Furthermore, in certain embodiments of the present invention, steps illustrated in FIG. 1 may be performed in parallel or sequentially.

Alternatively, the binding, coupling, linking, attaching, or association of the sperm-linker-DNA complex can also be accomplished in vivo. The linker and the DNA can first be coupled or bound together in vitro. Afterwards, this linker-DNA complex can be injected directly or indirectly into a male animal's testicles. PCT Publications WO 99/40213 and WO 97/11597 disclose procedures for injecting DNA into the testicles, and these publications are incorporated herein by reference.

An example of a linker-DNA complex is an antibody attached with DNA molecules where the antibody specifically recognizes certain surface epitopes on sperm cells. Because of the acidic characteristic of naked DNA, it can ionically associate, bind or, couple with an antibody that has basic or positively charged properties. However, the DNA-linker interaction is not limited to ionic interaction. The complex can also be crosslinked by UV light to form covalent bonds by well known methods in the art. Both the DNA and the linker can also be modified by methods known in the art. For example, the DNA can be biotinylated by adding biotinylated deoxynucleotides in a PCR reaction; the antibody can be modified or purchased with attached streptavidin, which binds tightly to the biotin on the DNA; or a secondary antibody, which is modified with streptavidin and recognizes the first antibody can also act as a secondary linker between the modified DNA and the first linker.

In obtaining antibody linker molecules, general methods well known in the art of antibody generating technology can be used. Whole sperm cells, partial sperm cells or specific sperm antigens can be used to immunize animals to obtain anti-sperm antibody. In the case of transgenic birds, antibodies can also be made by fractionating serum, egg white or yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol. For making a monoclonal antibody, spleen cells are isolated from the immunized animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", J Immunol Methods 242:159 (2000), and by Burton, D. R., "Phage display", Immunotechnology 1:87 (1995), the disclosures of which are incorporated herein by reference.

It is known in the art of infertility treatment that some sperm antibodies may inhibit fertilization, (Yan et al., Nakamura et al., Naz et al., Kim et al.). This phenomena has been studied in the field of infertility as a potential (albeit in no way universal) cause of infertility among some couples. However, even among infertile couples, antisperm antibodies are primarily associated with reduced fertility in couples presenting with unexplained infertility, with the prevalence being only about 10% in this latter group. In fact, sperm-specific antibodies, are often present in many fertile couples. Indeed, there are numerous studies confirming that sperm-specific antibodies do not inhibit fertilization. (Pagidas et al., Fertil. Steril., 62(2):363-9 (1994); Gleicher et al. *First World Conference: International Association of Private Assisted Reproductive Technology Clinics and Laboratories*, Venice, Italy, Mar. 13-18, 1999; Chiu et al., *Human Reproduction,* 17(4): 984-989 (2002).

In infertility treatment, the presence of anti-sperm antibodies as a potential cause of a couple's inability to conceive is considered only when other causes have been ruled out. It is a "last resort" diagnosis. It is estimated that sperm antibodies are a cause of infertility in only 1% of infertile couples. Thus, it remains unclear what, if any, role or significance can be attributed to naturally occurring sperm antibodies in inhibition of fertilization. Gleicher et al. supra, Chiu et al., supra. Until the present invention, the prior art has focused on diagnostic uses of sperm antibodies in unexplained infertility. Thus, until the present invention, the ability of sperm antibodies to aid in fertilization and in the transfer of exogenous DNA to a host cell was unknown. While one skilled in the art understood that there are some sperm-specific antibodies whose presence is correlated with a particular couple's infertility, the ability of sperm antibodies to successfully effect in vitro fertilization as well as the use of such antibodies as DNA linker molecules for effecting delivery of exogenous DNA into a host cell was unknown.

If the DNA-linker complex is injected into the testis of the animal, this complex can seek out the sperm cells and bind to them. Fertilization can then occur in vivo via either natural copulation of the male and female animals or by artificial insemination of the female with collected sperm cells. The collected sperm cells can also be used with in vitro fertilization techniques, which are well known in the art. On the other hand, if binding of the sperm-linker-DNA complex, as a whole, occurred in vitro, fertilization can be achieved by in vitro fertilization techniques. The fertilized eggs and resulting embryos can then be transplanted to hosts or surrogate-animal mothers for development. Alternatively, well known artificial insemination methods or injections of the sperm-linker-DNA complex directly into the oviduct of female animals can also achieve fertilization in vivo.

In certain embodiments, the invention may be used to introduce a nucleotide sequence of interest into an oocyte. Preferably, the nucleotide sequence is stably transformed into the embryonic cells), e.g., to create a transgenic animal such as a transgenic bird. Those skilled in the art will appreciate that it is not necessary that every cell of the resulting transgenic animal contain the transgene. The nucleotide sequence may be DNA or RNA, and it may encode any polypeptide of interest or may encode a non-translated RNA (e.g., antisense RNAs or ribozymes). In those embodiments wherein the nucleotide sequence encodes a polypeptide, the polypeptide may be a reporter polypeptide (e.g., an enzyme such as Green Fluorescent Protein or alkaline phosphatase), a therapeutic polypeptide, an immunogenic polypeptide (i.e., for vaccination), a growth or performance enhancing polypeptide, and the like.

The nucleotide sequence may be introduced into the embryo using any vector and method known in the art. For example, a viral vector (e.g., retrovirus) or DNA vector may be used to carry the exogenous nucleotide sequence of interest. In particular embodiments, a viral vector is not used to introduce the nucleotide sequence into the embryo. Instead, naked DNA may be introduced into a host cell or oocyte by use of the antibody-linkers.

Transgenic offspring may be detected by any of several means well known to those skilled in the art. Non-limiting examples include Southern blot or Northern blot analyses, using a probe that is complementary to at least a portion of the transgene. Western blot analysis using an antibody against the protein encoded by the transgene may be employed as an alternative or additional method for screening for the presence of the transgene product. A DNA sample may be prepared from a tissue or cell and analyzed by PCR for expression of the transgene.

Alternative or additional methods for evaluating the presence of the transgene include, without limitation, biochemical assays such as enzyme and/or immunological assays, histological stains for a particular marker or enzyme activity, flow cytometric analysis, in situ hybridization of mRNA analysis, and FACS analysis of protein expression. Analysis of the blood may also be useful to detect the presence of the transgene product in the blood, as well as to evaluate the effect of the transgene on the levels of various types of blood cells and other blood constituents.

Animal tissue may also be analyzed directly, for example, by preparing tissue sections. In some embodiments, it may be preferable to fix the tissue (e.g., with paraformaldehyde or formalin). Tissue sections may be prepared frozen, or may be paraffin-embedded. Slides of animal tissue may be used for immunohistochemistry, in vitro hybridization or histology (e.g., hematoxylin and eosin staining).

Transgenic cells, genetically identical cells, and stem cells derived from primates are invaluable for the study of numerous diseases (e.g., aging, AIDS, cancer, Alzheimer's disease, autoimmune diseases, metabolic disorders, obesity, organogenesis, psychiatric illnesses, and reproduction). Furthermore, the importance of these cells for molecular medicine and the development of innovative strategies for gene therapy protocols should not be minimized. For example, clinical strategies may include assisted reproductive technologies, transgenesis, and use of totipotent and immortalized embryonic germ (EG) and stem cells (ES). In addition, identical, transgenic and/or immortalized, totipotent EG or ES-derived cells may be ideal preclinical models in identifying the molecular events related to infertility, gametogenesis, contraception, assisted reproduction, the genetic basis of infertility, male versus female meiotic cell cycle regulation, reproductive aging, and the non-endocrine basis of idiopathic infertility.

Transgenesis may also be used to discover disease mechanisms and to create and optimize molecular medical cures.

The present invention also relates to methods of preparing and using transgenic embryonic cells, in particular to treat human diseases. Specifically, the methods to produce transgenic animals, described in the present invention, may also be used to create transgenic embryonic stem cells. Briefly, following fertilization, an egg divides over a period of days to form a blastocyst which, generally, is a hollow ball of cells having an inner cell mass and a fluid-filled cavity, both encapsulated by a layer of trophoblast cells. Cells from the inner cell mass of an embryo (i.e., blastocyst) may be used to derive a cell line referred to as embryonic stem cells (ESCs), and these cells may be maintained in tissue culture (see e.g., Schuldiner et al., 97 PROC. NATL. ACAD. Sci. USA 11307-12, 2000; Amit et al., 15 DEV. BIOL. 271-78, 2000; U.S. Pat. Nos. 5,843,789, 5,874,301). In general, stems cells are relatively undifferentiated, but may give rise to differentiated, functional cells. For example, hematopoietic stem cells may give rise to terminally differentiated blood cells such as erythrocytes and leukocytes.

Genetically modified animals can serve a number of useful applications. Livestock, poultry, or fish can be inserted with genes that encode for growth hormones to make them grow faster than normal or they can also be inserted with the somatotropin gene to increase muscle growth and decrease adipose tissue. Pursel, V. G., et. al. (1989) Genetic Engineering of Livestock, Science, Vol. 244, pp. 1281-1288; Etherton, T. D., et. al. (1993) Mechanism by which Somatotropin Decreases Adipose Tissue Growth, *American Journal of Clinical Nutrition*, Vol. 58 (Supp.), pp. 287S-295S. Inserting genes such as interferon that boost the immune system or other genes, such as genes encoding for viral, prion, or bacterial proteins, can also make these livestock, poultry, or fish disease or pathogen resistant. Examples of these infectious pathogens include *Salmonella*, influenza virus, prion proteins for the Mad Cow Disease, etc. Alternatively, introducing DNA encoding for anti-sense RNA molecules, which are complementary to these viral, prion, or bacterial RNAs, may also inhibit translation and production of proteins from these RNA, which limits growth and spread of these infectious pathogens.

Genetically modified avians are particularly useful as systems for protein production. Purification of proteins from transgenic chicken eggs is relatively simple and cost-effective. In addition, these systems are particularly well suited for large-scale production of therapeutic proteins.

Moreover, in animals, including insects such as silkworms, that produce raw materials for clothing such as wool and silk, inserting genes for biochemical enzymes that produce the rate-limiting amino acid may increase production of these raw materials. In sheep, for example, the availability of the amino-acid cysteine limits the production of wool. Inserting bacterial genes that encode for serine transacetylase and O-acetylserine sulfhydrylase may increase the conversion of serine and acetyl-CoA into cysteine, which in turn may increase production of wool. Ward, K., (1991) The Application of Transgenic Techniques for the Improvement of Domestic Animal Productivity, *Current Opinion in Biotechnology*, Vol. 2, pp. 834-839.

Furthermore, these genetically modified animals can also produce therapeutic proteins, such as insulin, growth hormone, interferon, erythropoietin, colony stimulating factor (GM-CSF), t-PA, or factor VIII, in their milk by joining the genes for these proteins with promoters from mammary specific genes such as sheep's β-lactoglobulin, mouse whey acid protein, or bovine αS1-casein. Id. On the other hand, the animal's milk can also be fortified with addition of humanized proteins, such as human lactoferrin that enhance the intestinal iron absorption in infants. Lonnerdal, B. (1996) Recombinant Human Milk Proteins—An Opportunity and a Challenge, *American Journal of Clinical Nutrition*, Vol. 63, pp. 622-626. Genetically modified pigs can even be a source for more "humanized" organs in animal to human xenotransplantation using genes such as human decay accelerating factor. Cozzi, E., et. al. (1994) Expression of Human Decay Accelerating Factor in Transgenics Pigs, *Transplantation Proceedings*, Vol. 26, pp. 1402-1403.

The following examples demonstrate that the inventor has produced a number of genetically modified animals using the sperm vector as described above. Methods in molecular genetics, flow cytometry, antibody production, hybridoma technology, in vitro fertilization, embryo manipulation, and artificial insemination used but not explicitly described in this disclosure had already been amply reported in the scientific literature. These methods are well within the ability of one skilled in the art.

EXAMPLE I

This example illustrates the preparation of an antibody specific to sperm cells.

Sperm cells collected from male mice were injected back into mice as antigens to immunize and produce antibodies reactive to sperm-surface antigens. Monoclonal antibodies, developed using common hybridoma techniques, were screened using flow cytometry to identify candidate antibodies that will bind to a series of different animals (mouse, pig, cow, sheep, goat, and chicken). Briefly, sperm cells were incubated with the different primary monoclonal antibodies, washed, and further incubated with a secondary antibody that specifically recognized mouse immunoglobulin. This secondary antibody, which was commercially available and well known in the art, had fluorescent molecules such as fluorescein or rhodamine conjugated to it. Once the secondary antibody molecules were bound and washed, the flow-cytometry instrument or the FACS sorter counted the number of fluorescent sperm cells with bound primary and secondary antibodies from naked sperm cells.

Figure 2:
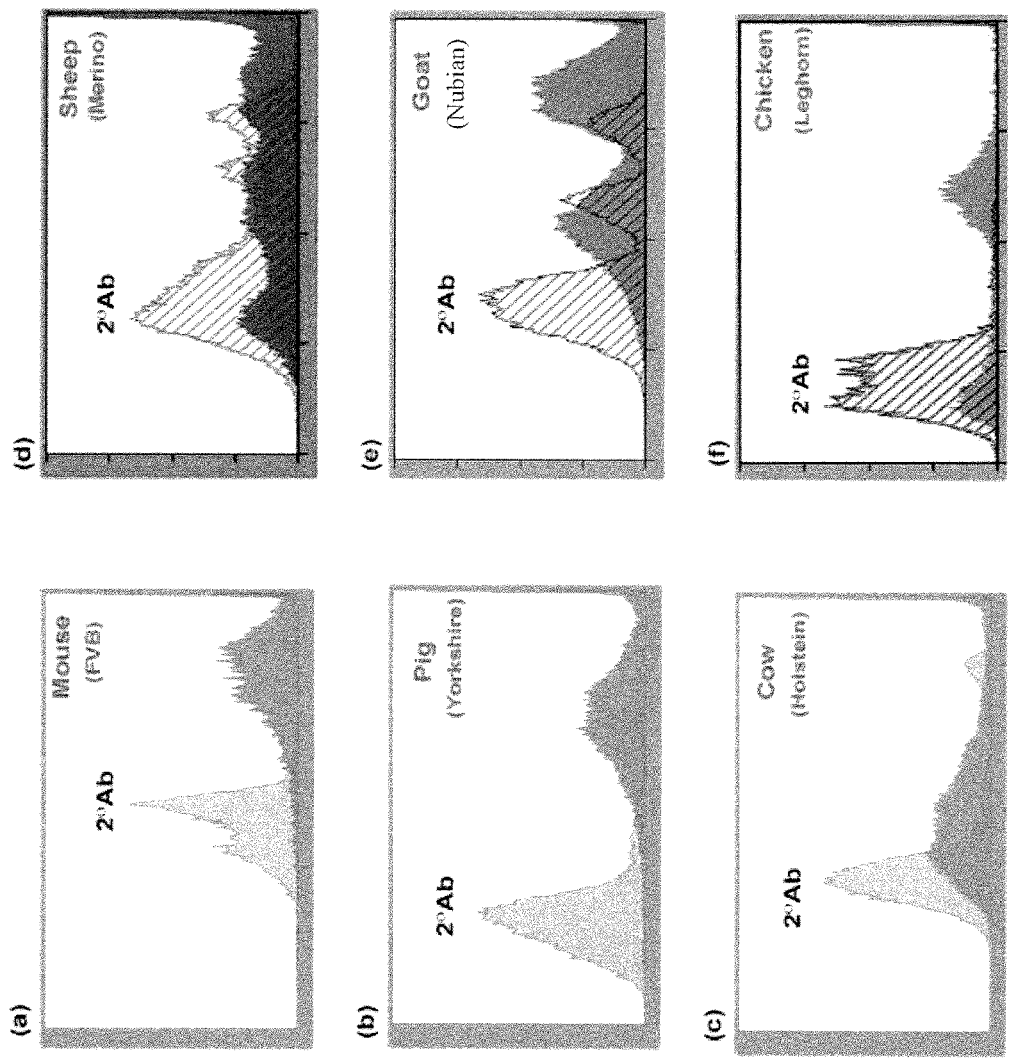
FIG. 2 shows a flow-cytometry result of binding a sperm-specific antibody to sperm cells from different animal species. (a) binding to mouse sperm cells as embodied in one aspect of the invention; (b) binding to pig sperm cells as embodied in one aspect of the invention; (c) binding to cow sperm cells as embodied in one aspect of the invention; (d) binding to sheep sperm cells as embodied in one aspect of the invention; (e) binding to goat sperm cells as embodied to one aspect of the invention; and (f) binding to chicken sperm cells as embodied in one aspect of the invention.

FIG. 2 shows the flow-cytometry analyses for mAbC that bind to sperm cells of mouse, pig, cow, sheep, goat and chicken. The Y-axis corresponds to the number of sperm cells detected while the X-axis is the relative intensity of fluorescence bound to the cell. Cross-lined peaks denote control reactions where the sperm cells were incubated only with the fluorescent anti-mouse immunoglobulin antibody. On the other hand, the shaded peaks denote the reactions where mAbC antibody and the secondary antibody were incubated with corresponding sperm cells in a mouse, pig, cow, chicken, goat, and sheep, respectively. Right shifts in the peaks denote positive binding of the mAbC antibody.

As can be seen in FIG. 2(a), greater fluorescence signals can be detected from mouse sperm cells incubated with mAbC and the fluorescent secondary antibody compared with sperm cells incubated with fluorescent secondary antibody alone. Similarly, in FIGS. 2(b) and 2(c), greater fluorescence can be detected from pig and cow sperm cells, respectively, incubated with mAbC and the fluorescent secondary antibody as evidenced by the right shaded peaks.

In FIG. 2(f), the incubation of the fluorescence antibody alone with the chicken sperm cells did not result in any fluorescence being detected in these sperm cells. In contrast, the right peak signified fluorescence in the chicken sperm cells that have attached mAbC antibodies. FIG. 2(f) also shows that some population of chicken sperm cells may not express the antigen recognized by mAbC as evidence by the left shaded peak.

In FIG. 2(e), fluorescence can be detected from goat sperm cells incubated with mAbC and the fluorescent secondary antibody as evidenced by the two right shaded peaks. The left shaded peak may suggest a population of the goat sperm cells that express the antigen recognized by mAbC at a lower level than the population in the right peak. In contrast with the chicken sperm cells incubated with only the fluorescent secondary antibody in FIG. 2(e), the anti-mouse immunoglobulin fluorescent antibody seems to also bind to the goat sperm cells, but at a much reduced level than with mAbC acting as a linker.

Similarly, in FIG. 2(d), fluorescence can be detected from sheep sperm cells incubated with mAbC and the fluorescent secondary antibody as evidenced by the right shaded peaks. The distribution of the peaks again suggests the possibility that different sperm cells have different levels of the antigen recognized by mAbC.

As seen in FIG. 2 mammalian sperm cells bind, at some lower level, to the fluorescent secondary antibody. Since the secondary antibody is directed to a mouse immunoglobulin, it may have cross reactivity to other mammalian proteins on the sperm cell surfaces, which are not present in the chicken sperm cells (FIG. 2(f)). Nevertheless, the shifts in fluorescence peaks upon addition of mAbC clearly demonstrate the higher affinity of the mAbC antibody to different animal sperm cells.

EXAMPLE II

This example illustrates the ability of the monoclonal antibody mAbC to bind to DNA molecules through ionic interaction.

Figure 3:
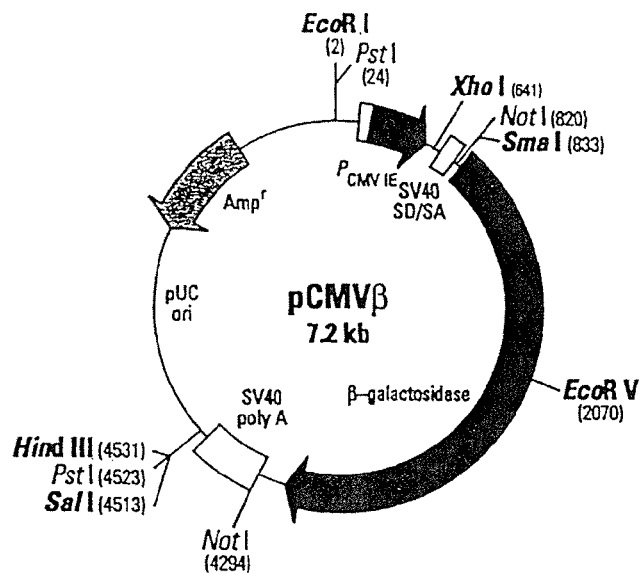
FIG. 3 shows a plasmid map of pCMV-β. Unique restriction sites are shown in bold type. pCMV-β is a mammalian reporter vector designed to express β-galactosidase in mammalian cells from the human cytomegalovirus immediate early gene promoter. pCMV-β contains an intron (splice donor/splice acceptor) and polyadenylation signal from SV40 and the full-length *E. coli*-galactosidase gene with eukaryotic translation initiation signals. pCMV-β expresses high levels of β-galactosidase and can be used as a reference (control) plasmid when transfecting other reporter gene constructs or to optimize transfection protocols by employing standard assays or stains to assay β-galactosidase activity. Alternatively, the β-galactosidase gene can be excised using the NotI sites at each end to allow other genes to be inserted into the pCMV-β vector backbone for expression in mammalian cells or to insert the β-galactosidase fragment into another expression vector.

Different volumes of purified solutions of mAbC at a concentration of 0.5 mg/ml were added to DNA solutions containing 300 ng of Sal I cut pCMV-β plasmid (FIG. 3, Clontech Laboratories, Inc., Cat. #6177-1). After incubating the mixtures at room temperature for forty minutes, the mixtures were loaded on a regular one percent agarose gel and run at 20 milli-amps for one hour. Afterwards, the DNA was stained with Ethidium Bromide and visualized under UV light.

Figure 4:
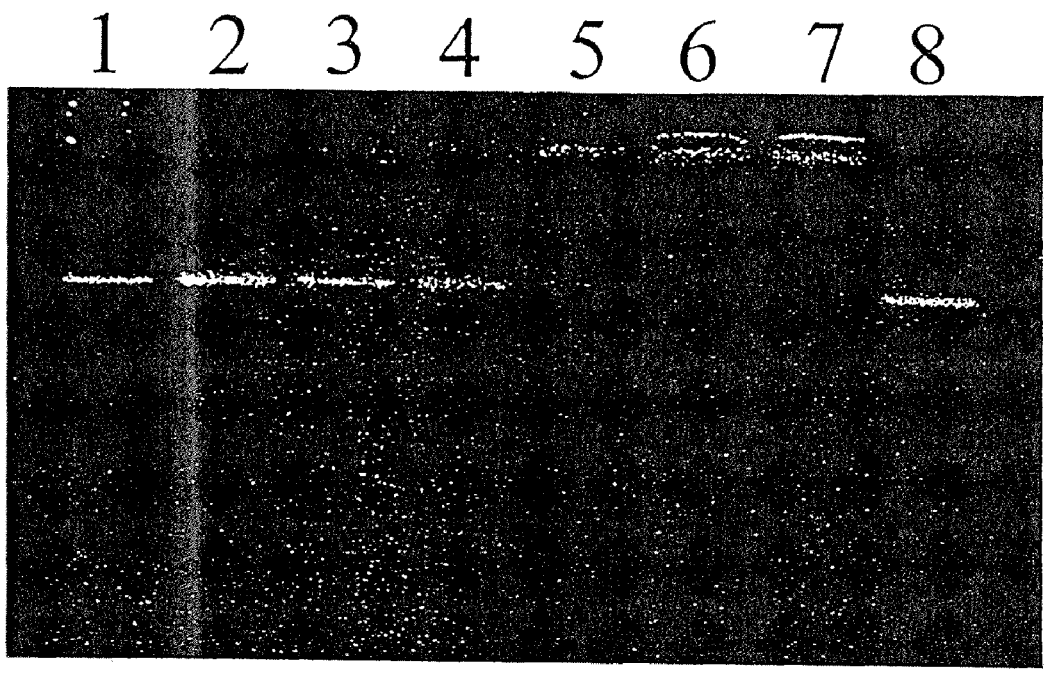
FIG. 4 shows an agarose-gel analysis of a sperm-specific antibody binding to pCMV-β plasmid.

In FIG. 4, lanes 1, 2, and 8 were controls with lane 1 being pure Sal I cut pCMV-β plasmid and lanes 2 and 8 being Sal I cut pCMV-β plasmid in Modified Tyrode's medium. Lanes 3, 4, 5, 6, and 7 corresponded to experimental reactions with the Sal I cut pCMV-β plasmid incubated with 0.2 µl, 1 µl, 2.5 µl, 6 µl, and 10 µl of mAbC at 0.5 mg/ml. In lanes 5, 6, and 7, increasing amounts of DNA were retained in the wells of the gel, showing that association of the antibody, which has a positive charge, with the plasmid DNA, which has a negative charge, yielded a net electric charge of zero, resulting in a complex that no longer responds to the electric field in the gel.

EXAMPLE III

This example illustrates the binding or coupling of the DNA to the sperm via the linker or antibody.

DNA molecules, labeled with $P^{32}$ using standard end labeling techniques with T4 DNA polymerase, were incubated with mouse, pig, chicken, sheep, goat, and cow sperm cells together with either mAbC, mAbD, or a control antibody specific to a *Drosophila* protein. The amount of DNA binding was measured by scintillation counting. The ratio of sperm cells to antibody were as follows:

Mouse—400 thousand sperm cells to 600 ng of labeled DNA;

Pig—600 thousand sperm cells to 800 ng labeled DNA;

Chicken—300 thousand sperm cells to 500 ng of labeled DNA;

Sheep—1 million sperm cells to 500 ng of labeled DNA;

Goat—1 million sperm cells to 500 ng of labeled DNA; and

Cow—1 million sperm cells to 500 ng of labeled DNA.

Table 1 shows that with the presence of mAbC and mAbD, sperm cells significantly bound more labeled DNA compared with reactions with no antibody or with the *Drosophila* protein-specific antibody. Reactions 1 and 2 contained only sperm cells and labeled DNA, while reactions 3 and 4 contained the *Drosophila*-protein-specific antibody together with sperm cells and labeled DNA. Reactions 5 contained mAbD while reactions 6 and 7 contained mAbC together with sperm cells and labeled DNA.

TABLE 1

| Reactions | | Mouse (cpm) | Pig (cpm) | Chicken (cpm) | Sheep (cpm) | Goat (cpm) | Cow (cpm) |
|---|---|---|---|---|---|---|---|
| 1 | no antibody | 12471 | 12971 | 5830 | 15367 | 17749 | 12766 |
| 2 | no antibody | 15814 | 13713 | 6383 | 13259 | 16574 | 14398 |
| 3 | Control Antibody | 11541 | 10531 | N/D | 14018 | 155347 | 15351 |
| 4 | Control Antibody | 13653 | 14038 | N/D | 12834 | 15997 | 13918 |
| 5 | mAbD | 18900 | 16220 | 10314 | N/D | N/D | N/D |
| 6 | mAbC | 18139 | 16269 | 7294 | 19368 | 20385 | 20417 |
| 7 | mAbC | 19314 | 17343 | 9865 | 18437 | 19543 | 18643 |

N/D = Not determined

EXAMPLE IV

This example illustrates the ability of numerous sperm specific antibodies to successfully effect in vitro fertilization of oocytes.

Sperm cells were collected from the epididymis of donor male mice as described above. The collected sperm cells were then used to immunize host female mice for production of anti-sperm antibodies using common hybridoma techniques and as described above. Screening assays were performed as follows to identify those hybridomas expressing antibodies which allow fertilization of oocytes and effect fertilization of the oocytes. Using the methods disclosed herein, antibodies able to specifically bind sperm cells and introduce exogenous DNA into an oocyte were reproducibly identified. Three hundred fifty-four hybridoma lines which express antibodies able to specifically bind sperm cells were identified. Seventeen of the 354 hybridomas expressed antibodies able to specifically bind to sperm and introduce exogenous DNA into an oocyte ("effect" fertilization of an oocyte). Using the methods disclosed herein, 4.8% of the anti-sperm antibodies allowed ("effected") fertilization of an oocyte and were useful for introducing exogenous DNA into the oocyte as well as subsequently generated zygote and progeny.

Oocytes were obtained from fifty supraovulated 8 week old B6D2F1 female mice by injection with pregnant mareserum gonadotropin (PMS obtained from Sigma). The mice were injected on day 1 intravenously. Forty-eight hours later (day 3), each mouse was injected I.V. with human chorionic gonadotropin (hCG). On day 4, the mice were sacrifice and cumulus cells containing oocytes were obtained from the swollen ampullas. The eggs were collected in MTM medium. Each cumulus mass containing oocyte was then distributed to a well (48-well dish) in 200 ul MTM media. On average, twenty oocytes were obtained per supraovulated mouse. Separately, twenty ul of supernatant from the anti-sperm hybridoma lines were added to $5\times10^4$ sperm cells in 30 ul MTM media for 30 minutes to allow binding of the anti-sperm antibodies to the sperm cells. The antibody-bound sperm were then added to the oocyte-containing wells and incubated at 37° C. for four hours to allow for in vitro fertilization. Fertilized eggs were then collected and transferred to CZB medium and further incubated for 20-22 hrs at 37° C. to allow for further growth. The fertilization efficiency was then observed. Fertilization efficiency was quantified as "+++" (Group 1) represent no blockage of fertilization by hybridoma supernatant; "++" indicates some reduction in fertilization efficiency (Group 2).

Table 2 shows that several anti-sperm antibody expressing hybridoma cell lines allowed fertilization of oocytes. As indicated in Table 2, supernatant from six different hybridoma lines (categorized as "Group 1") successfully effected in vitro fertilization of oocytes (indicated as 1B3, 1F5, 2D4, 2E8, 3C7, 4E7). Fertilization was not inhibited by the presence of the sperm-specific antibodies.

TABLE 2

| Group 1 (+++) | Group 2 (++) | Group 3 (+) |
|---|---|---|
| 1B3 | 1B8 | 1A4 |
| 1F5 | 1C4 | 1B5 |
| 2D4 | 1G10 | 1F6 |
| 2E8 | 2B1 | 2A10 |
| 3C7 | 2C8 | 2B2 |
| 4E7 | 2E2 | 2E3 |
|  | 2E4 | 2F4 |
|  | 3A7 | 3B7 |
|  | 3A10 | 3D4 |
|  | 3B8 | 4C8 |
|  | 3G2 | 4C9 |
|  | 3H6 |  |
|  | 4A8 |  |
|  | 4B4 |  |
|  | 4E3 |  |
|  | 4E8 |  |

The above assays were repeated twice and the results confirmed. Table 3 shows the results of in vitro fertilization assays in the presence of supernatant derived from secondary cultures (subclones) of the same hybridoma lines identified above as able to effect in vitro fertilization (Group I hybridomas; Table 2). The in vitro fertilization assay was performed once or twice for each subclone as indicated below the subclone identifier (for example, subclone 1A8 derived from hybridoma 1B3 successfully effected fertilization in two assays as indicated by "+++". As indicated in Table 3, supernatant from the subclones 1B3, 1F5, 2D4, 2E8, 3C7 and 4E7 successfully effected fertilization of oocytes. As indicated in Table 3, original hybridoma 1B3 (also indicated in Table 2) was used to produce subclones 1A8, 2A2 and 2E7 (indicated in Table 3); original hybridoma 1F5 (also indicated in Table 2) was used to produce subclones 1D8 and 1H4 (indicated in Table 3); original hybridoma 2D4 (also indicated in Table 2) was used to produce subclones 1F3, 1G4, 1G2, 1G9, 2B8 and 2C3 (indicated in Table 3); original hybridoma 2E8 (also indicated in Table 2) was used to produce subclones 2G5, 2G8 and 1C10 (indicated in Table 3); original hybridoma 3C7 (also indicated in Table 2) was used to produce subclones 2C5, 1D8, 2C6, and 2D10 (indicated in Table 3); and original hybridoma 4E7 (also indicated in Table 2) was used to produce subclones 1F11, 1B1, 1H2 and 2E8 (indicated in Table 3).

TABLE 3

| Group 1 | Subclone | Subclone | Subclone | Subclone | Subclone | Subclone |
|---|---|---|---|---|---|---|
| 1B3 | 1A8 (+++)/(+++) | 2A2 (+++)/(+++) | 2E7 (+++)/(+++) | | | |
| 1F5 | 1D8 ++/+ | 1H4 + | | | | |
| 2D4 | 1F3 +++/+ | 1G4 +++/+ | 1G2 ++ | 1G9 ++ | 2B8 ++ | 2C3 ++ |
| 2E8 | 2G5 +++/+++ | 2G8 +++/+++ | 1C10 ++/++ | | | |

TABLE 3-continued

| Group 1 | Subclone | Subclone | Subclone | Subclone | Subclone | Subclone |
|---|---|---|---|---|---|---|
| 3C7 | 2C5 | 1D8 | 2C6 | 2D10 | | |
| | ++/++ | ++/+ | ++/+ | ++/+ | | |
| 4E7 | 1F11 | 1B1 | 1H2 | 2E8 | | |
| | +++/+++ | ++/++ | ++/++ | ++/++ | | |

The hybridoma 1B3 was also then used to generate ascites fluid.

Specific binding of the fertilization-effecting antibodies to sperm cells was confirmed using flow cytometry (immunostaining assay and observe with fluorescent microscopy). Monoclonal antibodies derived from the hybridoma lines are also referred to herein as "mAbA (1B3); "mAbB" (2D4); "mAbC" (3C7); "mAbD" (2E8); "mAbE" (4E7); and "mAbF" (1F5). Flow cytometry analysis confirmed the ability of mAbA, mAbB, mAbC, mAbD, mAbE, and mAbF to specifically bind to sperm cells.

EXAMPLE V

This example illustrates the procedures carried out to generate genetically modified mice.

Sperm cells were collected from dissected epididymis of nine to twenty weeks old FVB male mice. Cut into small pieces, these epididymis tissues were incubated in 300% of Modified Tyrode's medium at pH 7~8 for one hour to allow the sperm cells to escape into the medium. Once the sperm cells were collected in 300% of medium, five micrograms of the linker antibody were added to one million sperm cells at 37° C. for one hour. The sperm-linker complex was washed three times with 300 μl of Modified Tyrode's medium using a standard microcentrifuge set at 3000 rpm for one and a half minutes. The sperm-linker complex was finally resuspended in 300% of medium, and one microgram of linearized pCMV-β plasmid or a plasmid encoding for Hepatitis B surface antigen (HBsAg) was added and incubated for one hour.

To collect ovulated eggs, nine to twelve weeks FVB female mice each received an injection of 5 I.U. Pregnant Mares Serum (PMS) four days before the collection date and another 5 I.U. of human chorionic gonadotropin (hCG) two days before the collection date. Dissected ovulated eggs surrounded by cumulus cells were placed in a 35-mm petri dish containing a drop of Modified Tyrode's medium at room temperature. Afterwards, 300 μl of sperm-linker-DNA complex prepared as described above were added directly to the ovulated eggs. The whole mix was equilibrated with $CO_2$ at 37° C. with mineral oil added on top to prevent evaporation. After four hours of in vitro fertilization at 37° C., fertilized eggs were collected with capillary tubes and washed thrice with CZB medium. The embryos were further incubated in 300% of CZB medium for 20-22 hrs before being transferred to oviducts of pseudo-pregnant female mice.

Figure 5:
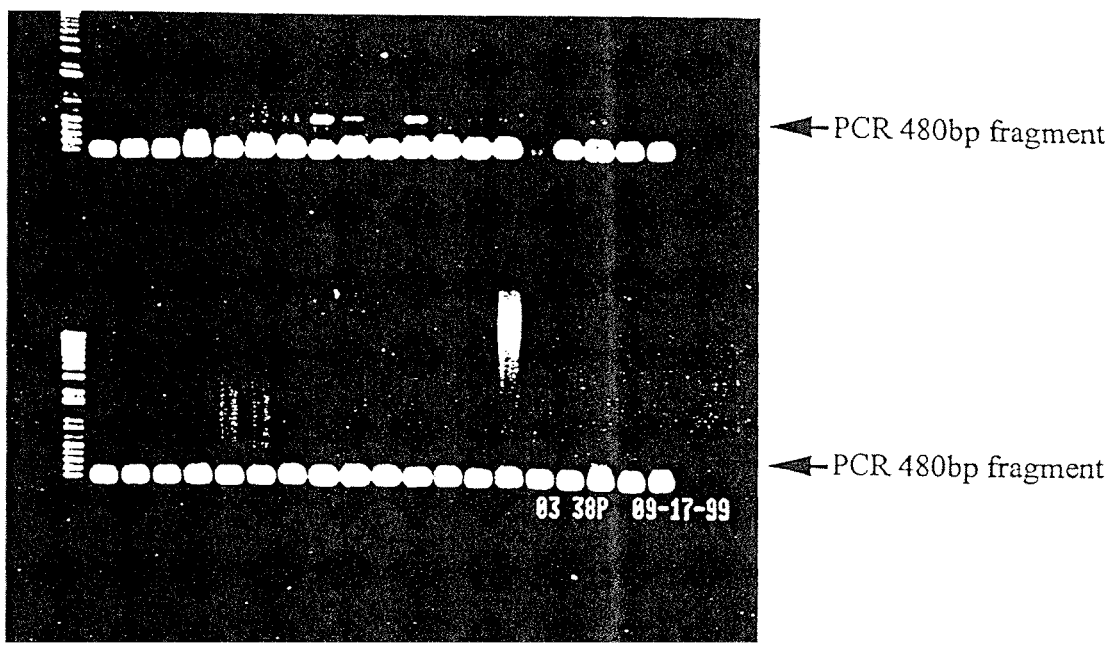
FIG. 5 show results of PCR analysis for the detection of pCMV-β sequences in genomic DNA isolated from mice embryos genetically modified according to basic steps outlined in FIG. 1.

To confirm the presence of the pCMV-β plasmid, genomic DNA isolated from embryos, ten days after transplantation into the pseudo-pregnant female mice, were analyzed by PCR using primers that detect a 480 bp fragment corresponding to the CMV promoter region of the pCMV-β plasmid (FIG. 3). In FIG. 5, lanes 6, 7, 8, 9, 10, 12, 13, 14, 15, 17, 18, 19, 24, 33, and 40 clearly show this 480 bp PCR fragment. Lanes 1 and 21 corresponded to the molecular size markers.

Figure 6:
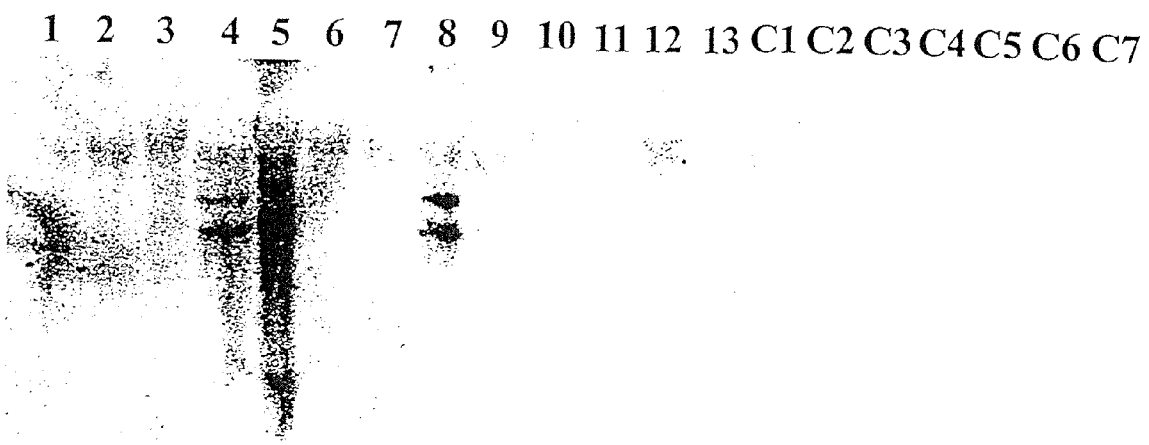
FIG. 6 shows results of Southern-blot analysis for the detection of Hepatitis B surface-antigen gene sequence integrated into mice genomic DNA according to one embodiment of the present invention.

To confirm integration of the HBsAg plasmid into the mice genome, southern blot analysis were also performed. Genomic DNA isolated from mice's tails were digested, ran on a gel, transferred to a nylon membrane according to methods known in the art. FIG. 6 shows the southern blot hybridization results with complementary probe sequences to HBsAg. Lanes 1-13 contained genomic DNA from mice born from pseudo-pregnant mice that received embryos fertilized with the sperm-linker-DNA complex described above; lanes C1-C7 contained genomic DNA from mice that were untreated or non-transgenic mice. Lanes 4, 5, and 8 show bands positive for HBsAg sequences integrated in the mice's genome, thus, demonstrating that three out the thirteen mice were genetically modified.

EXAMPLE VI

This example illustrates the procedures carried out to generate genetically modified pigs.

Ejaculated sperm cells from pigs were collected using methods generally known in the art of animal husbandry. Suspended in one milliliter of pig extender medium (purchased from Merck, Germany, Ref.N.R.13515/0001—dilute mixture M3 for boar sperm), fifteen million sperm cells were incubated with five micrograms of the linker antibody for forty minutes at room temperature with intermittent shaking in between. After washing the sperm-linker mixture once with pig extender medium and finally resuspending the mixture in 1.5 ml of the same medium, five micrograms of the plasmid pSEAP2-control (FIG. 7, Clontech Laboratories, Inc., Cat. #6052-1) were added and incubated with the mixture for forty minutes at room temperature. Direct injections of 200 μl of the resulting sperm-linker-DNA complex into the oviducts of anesthetized female pigs resulted in fertilization in vivo.

Figure 8:
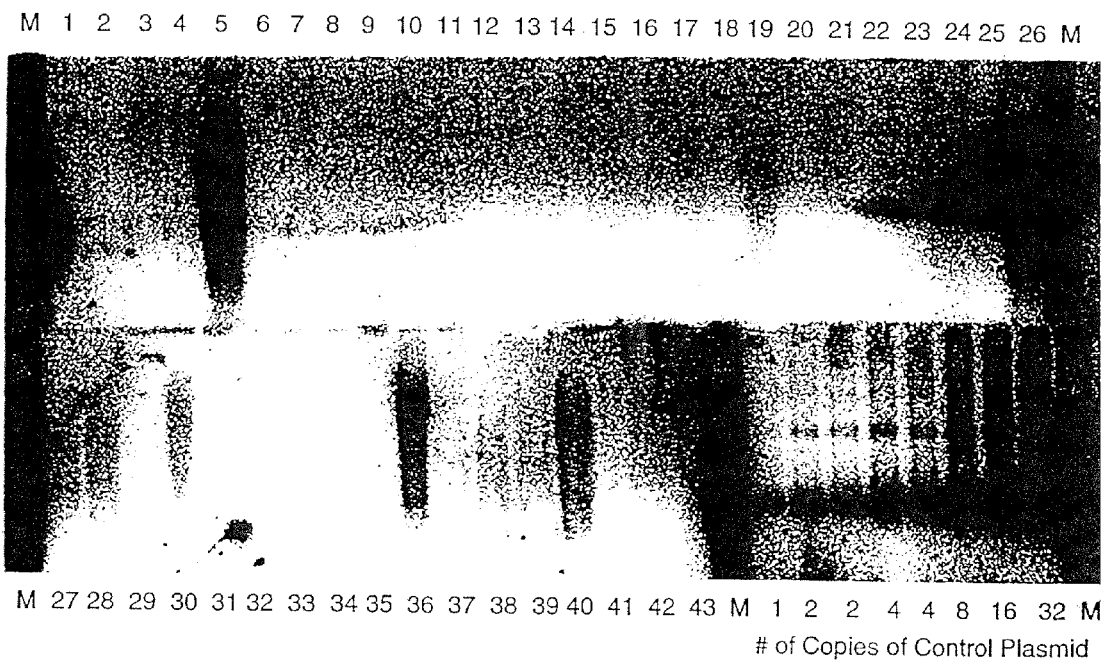
FIG. 8 shows the result of southern-blot analysis for the detection of pSEAP2-control plasmid sequence in the genomic DNA isolated from tail tissues of genetically modified pigs according to one embodiment of the present invention.
Figure 9:
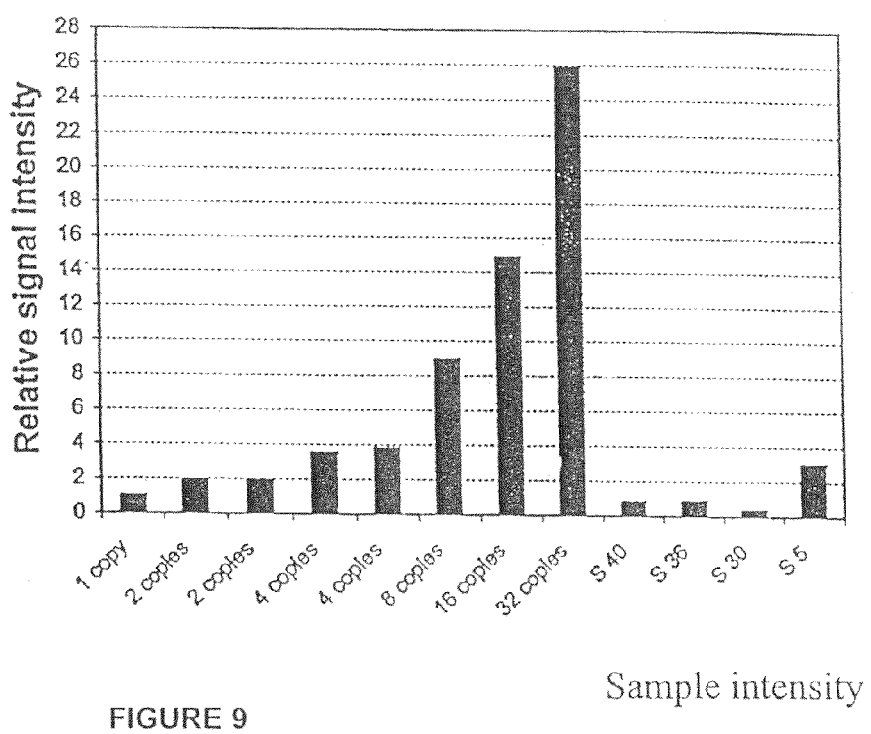
FIG. 9 shows the copy number of integrated pSEAP2-control plasmid in four genetically modified pigs based on densitometric intensities of bands in FIG. 8.

After the pigs were born and grown to 70-day-old pigs, they were analyzed for the presence of the pSEAP2-control plasmid. FIG. 8 shows the southern blot analysis of genomic DNA isolated from the tail tissues of these pigs. Briefly, genomic DNA isolated from these pigs were digested, run on a gel, and transferred to a nylon membrane according to methods well known in the art. The blot was then probed with labeled sequences from the Not I to BamH I region of the pSEAP2-control plasmid shown in FIG. 7. In FIG. 8, M denotes the marker lanes, and 1-43 denotes the number of pigs analyzed. Hybridization signals in lanes 5, 17, 19, 25, 26, 27, 28, 30, 36, 38, 39, and 40 indicated that the pSEAP2-control plasmid had integrated into the corresponding pig's genome. In the lower right half of the figure, eight lanes with increasing copies of pSEAP2-control plasmid molecules (1, 2, 2, 4, 4, 8, 16, and 32) were also loaded on the gel together with the DNA from the experimental pigs. These eight lanes were used to estimate the copy number of pSEAP2-control plasmid integrated into the pigs based on the densitometric intensities of the bands (FIG. 9). As can be seen in FIG. 9, S5 had the highest intensity, which corresponds to lane 5 of FIG. 8.

Figure 10:
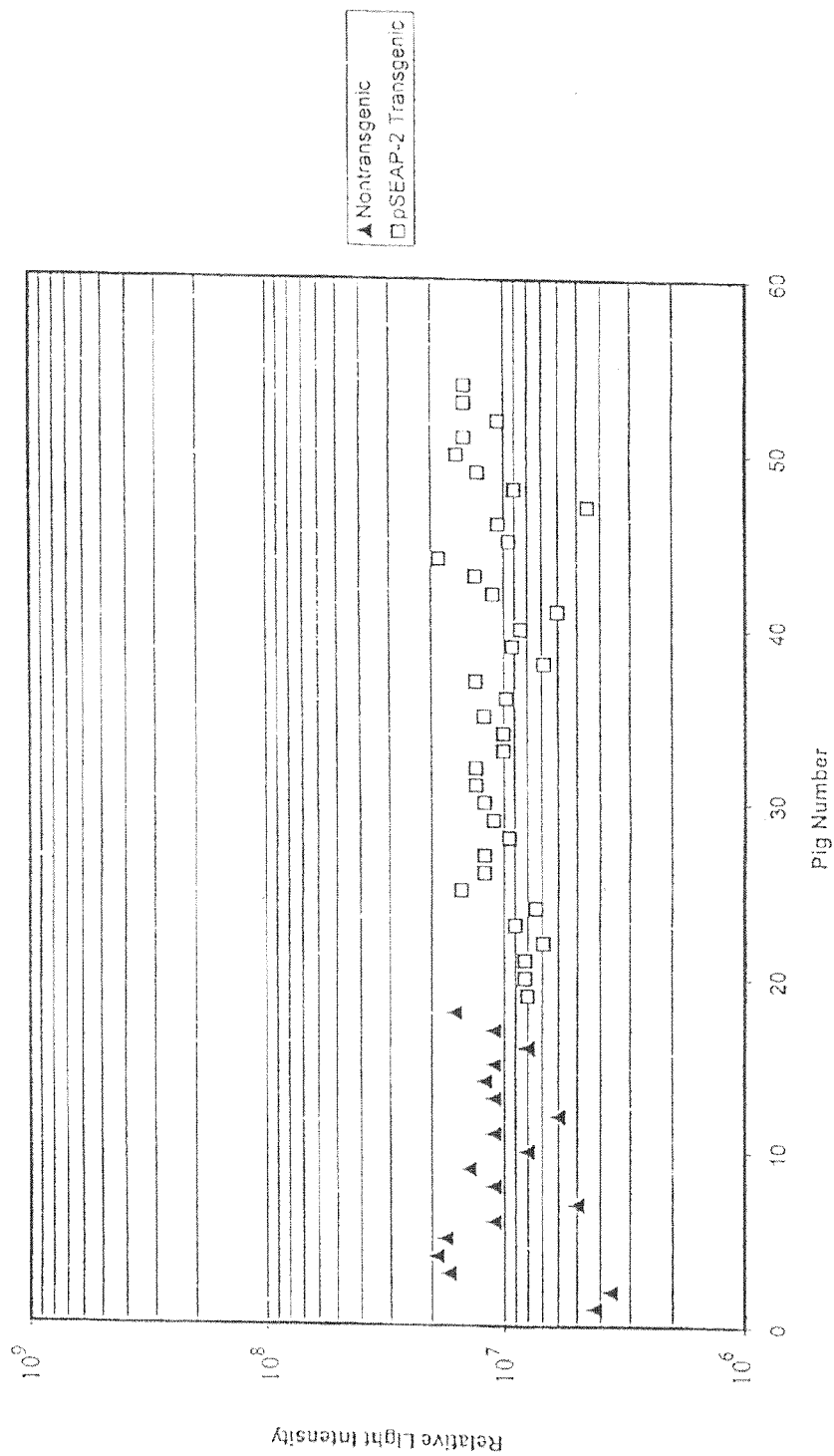
FIGS. 10 and 11 show the results of enzyme assays for secreted alkaline phosphatase found in serum of pigs genetically modified according to one embodiment of the present invention.
Figure 11:
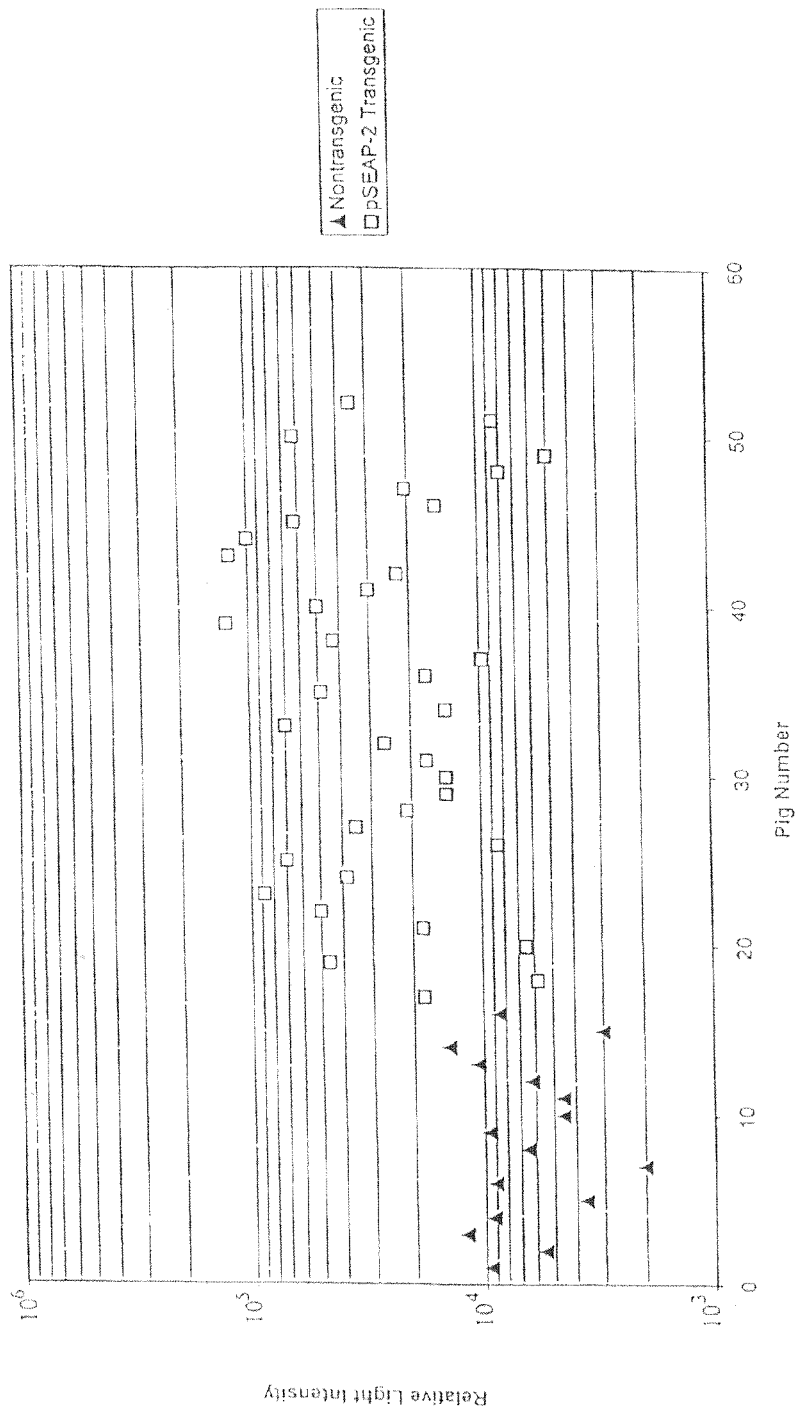

In another study, secreted alkaline phosphatase (SEAP) expressed from the pSEAP2-control plasmid were also detected in 70-day old genetically modified pigs. Serum from these pigs were collected and assayed for SEAP activity using Clontech's Great EscAPE™ SEAP Chemiluminescence Detection Kit (Cat. # K2041-1) and its protocol, which is incorporated herein by reference. The SEAP enzyme expressed from Clontech's pSEAP-2 vector is thermostable. Thus, to determine the level of SEAP activity as opposed to the pigs' endogenous alkaline phosphatase enzyme activity, the assay required the deactivation of the endogenous alkaline phosphatase enzyme by heating the samples at 65° C. for thirty minutes before adding the chemiluminescence substrate. As a control, FIG. 10 shows the result of the assay without performing this heat deactivation step. The level of total alkaline phosphatase activity was not significantly different between the genetically modified pigs and non-transgenic control pigs. In contrast, FIG. 11 shows the result including this heat deactivation step. Without the endogenous alkaline phosphatase activity, SEAP activity was significantly higher in the genetically modified pigs than in the non-transgenic control pigs. Thus, the pSEAP2-control plasmid had integrated well in the pigs' genome and was actively expressing the SEAP enzyme.

EXAMPLE VII

This example illustrates the procedures carried out to generate genetically modified chicken.

Generation of transgenic chicken (Linker Based Sperm Mediated Gene Transfer, "LB-SMGT"). Chicken semen was collected using methods generally known in the art of animal husbandry. The concentration of sperm was adjusted to 100× $10^8$ sperm in 1 ml final volume with extender. Sperm antibody (25 µg) was added to the sperm mixture and incubated for 30 minutes at room temperature with gentle shaking. The sperm-antibody mixture was centrifuged and supernatant removed. Extender was added to wash and the mixture spun again and supernatant removed. The pellet was resuspended with extender and 50 micrograms of the pGL3-control DNA was added. (pGL3 vector was obtained from Promega Corporation, Madison Wis.). The pGL3 vector sequence information is indicated below. The sperm-antibody-DNA mixture was incubated for one hour at room temperature with gentle shaking. Additional extender was added and female hens artificially inseminated using the sperm-antibody-DNA mixture.

Figure 12:
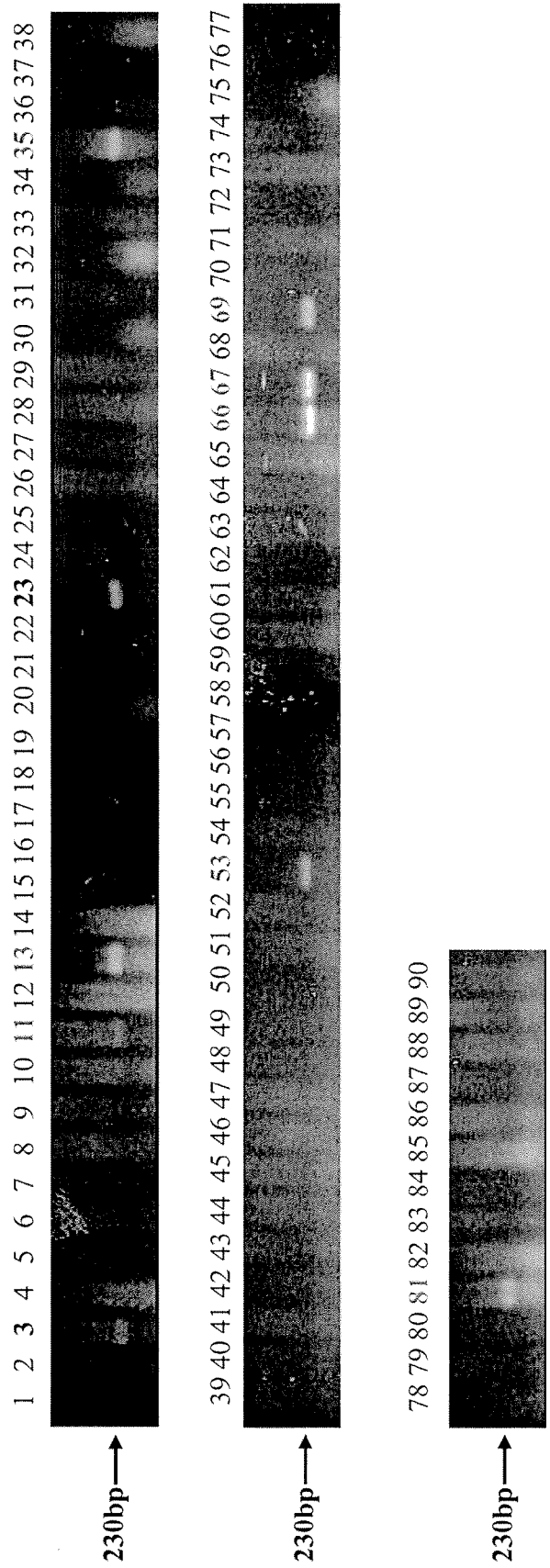
FIG. 12 shows the results of PCR analysis for the detection of pGL-3 control DNA sequences (230 bp) in genomic DNA isolated from transgenic chicken embryos (F0 generation) genetically modified according to basic steps in FIG. 1.

The presence of pGL3-control DNA [SEQ ID NO:1] in transgenic chicken embryos (F0 generation) was assayed by PCR. In FIG. 12, the expected amplification product is indicated (230 bp) by arrows. 1-90 denotes the number of embryos analyzed. Amplification product in lanes 3, 11, 13, 23, 35, 53, 66, 67, 69, 81 indicated that the pGL3-control DNA transgene was present in the embryos. As shown in FIG. 12, 12% of the F0 generation chicken embryos obtained from fertilization by DNA-sperm antibody linker-bound rooster sperm contained transgene.

The pGL3 sequence [SEQ ID NO: 1] and location of PCR primers is indicated below:

```
   1 GGTACCGAGC TCTTACGCGT GCTAGCCCGG GCTCGAGATC TGCGATCTGC

51 ATCTCAATTA GTCAGCAACC ATAGTCCCGC CCCTAACTCC GCCCATCCCG

101 CCCCTAACTC CGCCCAGTTC CGCCCATTCT CCGCCCCATC GCTGACTAAT

151 TTTTTTTATT TATGCAGAGG CCGAGGCCGC CTCGGCCTCT GAGCTATTCC

201 AGAAGTAGTG AGGAGGCTTT TTTGGAGGCC TAGGCTTTTG CAAAAAGCTT

251 GGCATTCCGG TACTGTTGGT AAAGCCACCA TGGAAGACGC CAAAAACATA

301 AAGAAAGGCC CGGCGCCATT CTATCCGCTG GAAGATGGAA CCGCTGGAGA

351 GCAACTGCAT AAGGCTATGA AGAGATACGC CCTGGTTCCT GGAACAATTG

Luc 1
          →
 401 CTTTTACAGA TGCACATATC GAGGTGGACA TCACTTACGC TGAGTACTTC

451 GAAATGTCCG TTCGGTTGGC AGAAGCTATG AAACGATATG GGCTGAATAC

501 AAATCACAGA ATCGTCGTAT GCAGTGAAAA CTCTCTTCAA TTCTTTATGC

551 CGGTGTTGGG CGCGTTATTT ATCGGAGTTG CAGTTGCGCC CGCGAACGAC

601 ATTTATAATG AACGTGAATT GCTCAACAGT ATGGGCATTT CGCAGCCTAC
                      ←
              Luc2

651 CGTGGTGTTC GTTTCCAAAA AGGGGTTGCA AAAAATTTTG AACGTGCAAA

701 AAAAGCTCCC AATCATCCAA AAAATTATTA TCATGGATTC TAAAACGGAT

751 TACCAGGGAT TTCAGTCGAT GTACACGTTC GTCACATCTC ATCTACCTCC

801 CGGTTTTAAT GAATACGATT TTGTGCCAGA GTCCTTCGAT AGGGACAAGA

851 CAATTGCACT GATCATGAAC TCCTCTGGAT CTACTGGTCT GCCTAAAGGT

901 GTCGCTCTGC CTCATAGAAC TGCCTGCGTG AGATTCTCGC ATGCCAGAGA

951 TCCTATTTTT GGCAATCAAA TCATTCCGGA TACTGCGATT TTAAGTGTTG

1001 TTCCATTCCA TCACGGTTTT GGAATGTTTA CTACACTCGG ATATTTGATA
```

```
1051  TGTGGATTTC GAGTCGTCTT AATGTATAGA TTTGAAGAAG AGCTGTTTCT

1101  GAGGAGCCTT CAGGATTACA AGATTCAAAG TGCGCTGCTG GTGCCAACCC

1151  TATTCTCCTT CTTCGCCAAA AGCACTCTGA TTGACAAATA CGATTTATCT

1201  AATTTACACG AAATTGCTTC TGGTGGCGCT CCCCTCTCTA AGGAAGTCGG

1251  GGAAGCGGTT GCCAAGAGGT TCCATCTGCC AGGTATCAGG CAAGGATATG

1301  GGCTCACTGA GACTACATCA GCTATTCTGA TTACACCCGA GGGGGATGAT

1351  AAACCGGGCG CGGTCGGTAA AGTTGTTCCA TTTTTTGAAG CGAAGGTTGT

1401  GGATCTGGAT ACCGGGAAAA CGCTGGGCGT TAATCAAAGA GGCGAACTGT

1451  GTGTGAGAGG TCCTATGATT ATGTCCGGTT ATGTAAACAA TCCGGAAGCG

1501  ACCAACGCCT TGATTGACAA GGATGGATGG CTACATTCTG GAGACATAGC

1551  TTACTGGGAC GAAGACGAAC ACTTCTTCAT CGTTGACCGC CTGAAGTCTC

1601  TGATTAAGTA CAAAGGCTAT CAGGTGGCTC CCGCTGAATT GGAATCCATC

1651  TTGCTCCAAC ACCCCAACAT CTTCGACGCA GGTGTCGCAG GTCTTCCCGA

1701  CGATGACGCC GGTGAACTTC CCGCCGCCGT TGTTGTTTTG GAGCACGGAA

1751  AGACGATGAC GGAAAAAGAG ATCGTGGATT ACGTCGCCAG TCAAGTAACA

1801  ACCGCGAAAA AGTTGCGCGG AGGAGTTGTG TTTGTGGACG AAGTACCGAA

1851  AGGTCTTACC GGAAAACTCG ACGCAAGAAA AATCAGAGAG ATCCTCATAA

1901  AGGCCAAGAA GGGCGGAAAG ATCGCCGTGT AATTCTAGAG TCGGGCGGC

1951  CGGCCGCTTC GAGCAGACAT GATAAGATAC ATTGATGAGT TTGGACAAAC

2001  CACAACTAGA ATGCAGTGAA AAAAATGCTT TATTTGTGAA ATTTGTGATG

2051  CTATTGCTTT ATTTGTAACC ATTATAAGCT GCAATAAACA AGTTAACAAC

2101  AACAATTGCA TTCATTTTAT GTTTCAGGTT CAGGGGGAGG TGTGGGAGGT

2151  TTTTTAAAGC AAGTAAAACC TCTACAAATG TGGTAAAATC GATAAGGATC

2201  TGAACGATGG AGCGGAGAAT GGGCGGAACT GGGCGGAGTT AGGGGCGGGA

2251  TGGGCGGAGT TAGGGGCGGG ACTATGGTTG CTGACTAATT GAGATGCATG

2301  CTTTGCATAC TTCTGCCTGC TGGGGAGCCT GGGGACTTTC CACACCTGGT

2351  TGCTGACTAA TTGAGATGCA TGCTTTGCAT ACTTCTGCCT GCTGGGGAGC

2401  CTGGGGACTT TCCACACCCT AACTGACACA CATTCCACAG CGGATCCGTC

2451  GACCGATGCC CTTGAGAGCC TTCAACCCAG TCAGCTCCTT CCGGTGGGCG

2501  CGGGGCATGA CTATCGTCGC CGCACTTATG ACTGTCTTCT TTATCATGCA

2551  ACTCGTAGGA CAGGTGCCGG CAGCGCTCTT CCGCTTCCTC GCTCACTGAC

2601  TCGCTGCGCT CGGTCGTTCG GCTGCGGCGA GCGGTATCAG CTCACTCAAA

2651  GGCGGTAATA CGGTTATCCA CAGAATCAGG GGATAACGCA GGAAAGAACA

2701  TGTGAGCAAA AGGCCAGCAA AAGGCCAGGA ACCGTAAAAA GGCCGCGTTG

2751  CTGGCGTTTT TCCATAGGCT CCGCCCCCCT GACGAGCATC ACAAAAATCG

2801  ACGCTCAAGT CAGAGGTGGC GAAACCCGAC AGGACTATAA AGATACCAGG

2851  CGTTTCCCCC TGGAAGCTCC CTCGTGCGCT CTCCTGTTCC GACCCTGCCG

2901  CTTACCGGAT ACCTGTCCGC CTTTCTCCCT TCGGGAAGCG TGGCGCTTTC

2951  TCATAGCTCA CGCTGTAGGT ATCTCAGTTC GGTGTAGGTC GTTCGCTCCA

3001  AGCTGGGCTG TGTGCACGAA CCCCCCGTTC AGCCCGACCG CTGCGCCTTA

3051  TCCGGTAACT ATCGTCTTGA GTCCAACCCG GTAAGACACG ACTTATCGCC
```

```
3101 ACTGGCAGCA GCCACTGGTA ACAGGATTAG CAGAGCGAGG TATGTAGGCG

3151 GTGCTACAGA GTTCTTGAAG TGGTGGCCTA ACTACGGCTA CACTAGAAGA

3201 ACAGTATTTG GTATCTGCGC TCTGCTGAAG CCAGTTACCT TCGGAAAAAG

3251 AGTTGGTAGC TCTTGATCCG GCAAACAAAC CACCGCTGGT AGCGGTGGTT

3301 TTTTTGTTTG CAAGCAGCAG ATTACGCGCA GAAAAAAGG ATCTCAAGAA

3351 GATCCTTTGA TCTTTTCTAC GGGGTCTGAC GCTCAGTGGA ACGAAAACTC

3401 ACGTTAAGGG ATTTTGGTCA TGAGATTATC AAAAAGGATC TTCACCTAGA

3451 TCCTTTTAAA TTAAAAATGA AGTTTTAAAT CAATCTAAAG TATATATGAG

3501 TAAACTTGGT CTGACAGTTA CCAATGCTTA ATCAGTGAGG CACCTATCTC

3551 AGCGATCTGT CTATTTCGTT CATCCATAGT TGCCTGACTC CCCGTCGTGT

3601 AGATAACTAC GATACGGGAG GGCTTACCAT CTGGCCCCAG TGCTGCAATG

3651 ATACCGCGAG ACCCACGCTC ACCGGCTCCA GATTTATCAG CAATAAACCA

3701 GCCAGCCGGA AGGGCCGAGC GCAGAAGTGG TCCTGCAACT TTATCCGCCT

3751 CCATCCAGTC TATTAATTGT TGCCGGGAAG CTAGAGTAAG TAGTTCGCCA

3801 GTTAATAGTT TGCGCAACGT TGTTGCCATT GCTACAGGCA TCGTGGTGTC

3851 ACGCTCGTCG TTTGGTATGG CTTCATTCAG CTCCGGTTCC CAACGATCAA

3901 GGCGAGTTAC ATGATCCCCC ATGTTGTGCA AAAAAGCGGT TAGCTCCTTC

3951 GGTCCTCCGA TCGTTGTCAG AAGTAAGTTG GCCGCAGTGT TATCACTCAT

4001 GGTTATGGCA GCACTGCATA ATTCTCTTAC TGTCATGCCA TCCGTAAGAT

4051 GCTTTTCTGT GACTGGTGAG TACTCAACCA AGTCATTCTG AGAATAGTGT

4101 ATGCGGCGAC CGAGTTGCTC TTGCCCGGCG TCAATACGGG ATAATACCGC

4151 GCCACATAGC AGAACTTTAA AAGTGCTCAT CATTGGAAAA CGTTCTTCGG

4201 GGCGAAAACT CTCAAGGATC TTACCGCTGT TGAGATCCAG TTCGATGTAA

4251 CCCACTCGTG CACCCAACTG ATCTTCAGCA TCTTTTACTT TCACCAGCGT

4301 TTCTGGGTGA GCAAAAACAG GAAGGCAAAA TGCCGCAAAA AAGGGAATAA

4351 GGGCGACACG GAAATGTTGA ATACTCATAC TCTTCCTTTT TCAATATTAT

4401 TGAAGCATTT ATCAGGGTTA TTGTCTCATG AGCGGATACA TATTTGAATG

4451 TATTTAGAAA AATAAACAAA TAGGGGTTCC GCGCACATTT CCCCGAAAAG

4501 TGCCACCTGA CGCGCCCTGT AGCGGCGCAT TAAGCGCGGC GGGTGTGGTG

4551 GTTACGCGCA GCGTGACCGC TACACTTGCC AGCGCCCTAG CGCCCGCTCC

4601 TTTCGCTTTC TTCCCTTCCT TTCTCGCCAC GTTCGCCGGC TTTCCCCGTC

4651 AAGCTCTAAA TCGGGGCTC CCTTTAGGGT TCCGATTTAG TGCTTTACGG

4701 CACCTCGACC CCAAAAAACT TGATTAGGGT GATGGTTCAC GTAGTGGGCC

4751 ATCGCCCTGA TAGACGGTTT TTCGCCCTTT GACGTTGGAG TCCACGTTCT

4801 TTAATAGTGG ACTCTTGTTC CAAACTGGAA CAACACTCAA CCCTATCTCG

4851 GTCTATTCTT TTGATTTATA AGGGATTTTG CCGATTTCGG CCTATTGGTT

4901 AAAAAATGAG CTGATTTAAC AAAAATTTAA CGCGAATTTT AACAAAATAT

4951 TAACGCTTAC AATTTGCCAT TCGCCATTCA GGCTGCGCAA CTGTTGGGAA

5001 GGGCGATCGG TGCGGGCCTC TTCGCTATTA CGCCAGCCCA AGCTACCATG

5051 ATAAGTAAGT AATATTAAGG TACGGGAGGT ACTTGGAGCG GCCGCAATAA
```

```
5101 AATATCTTTA TTTTCATTAC ATCTGTGTGT TGGTTTTTTG TGTGAATCGA

5151 TAGTACTAAC ATACGCTCTC CATCAAAACA AAACGAAACA AAACAAACTA

5201 GCAAAATAGG CTGTCCCCAG TGCAAGTGCA GGTGCCAGAA CATTTCTCTA

5251 TCGATA
```

PCR primers used to generate a 230 bp fragment were:

```
Primer 1 - Luc1 (upper primer at #404 underlined):
5' TTA GAG ATG CAC ATA TCG AG 3'    [SEQ ID NO: 2]

Primer 2 - Luc2 (lower primer at #614 underlined):
5' CAT ACT GTT GAG CAA TTC AC 3'    [SEQ ID NO: 3]
```

Figure 13:
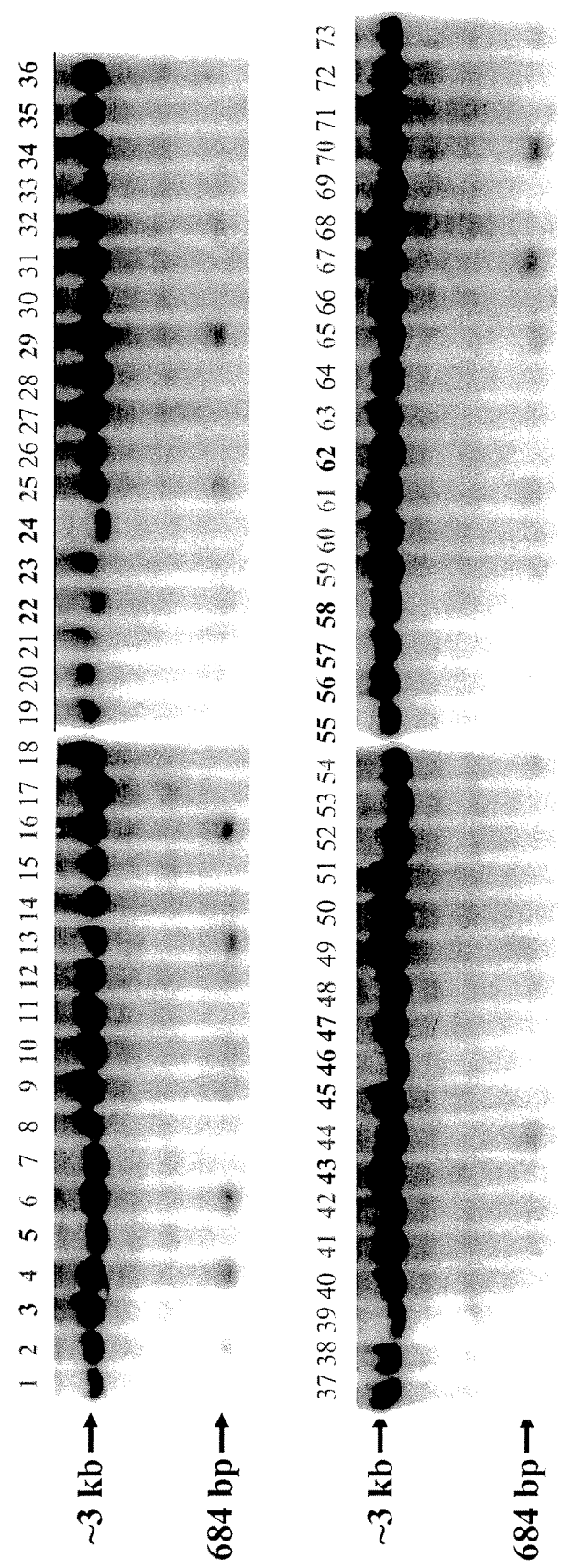
FIG. 13 shows the results of Southern-blot analysis for the detection of human Interferon-β sequence (684 b.p.) in genomic DNA isolated from second generation (F1 progeny) transgenic chicken embryos obtained from mating F0 transgenic hens with wild type roosters.

In a further study, using human interferon-β gene as exogenous DNA, fertilized chicken eggs were obtained using the above-described methods and F0 transgenic hens generated. The nucleic acid sequence of human interferon-β is indicated in FIG. 16. Randomly selected F0 transgenic hens having human interferon-β transgene were then mated with wild type roosters and the second generation (F1 generation) chicken embryos analyzed for presence of human interferon β transgene. Seventy-three chicken embryos obtained by these matings were analyzed by Southern Blot analysis for the presence of the exogenous DNA (human interferon-β transgene). Briefly, genomic DNA isolated from these embryos were digested, run on a gel, and transferred to a nylon membrane according to methods well known in the art. The blot was then probed with labeled sequences from the human interferon β gene. As shown in FIG. 13, "~3 kb" denotes the marker band (endogenous chicken lactin gene), and 1-73 denotes the number of embryos analyzed. The 684 bp insert of human interferon-β gene as denoted by arrow indicated that the human interferon β gene had integrated into the corresponding chicken embryo's genome. (Southern blot analysis was performed by digesting chicken genomic DNA with restriction enzyme, gel-electrophoresed and membrane blotted. The 684 bp represents human interferon-β gene integrated into chicken genomic DNA with additional 5'- and 3'-end sequence).

Figure 14:
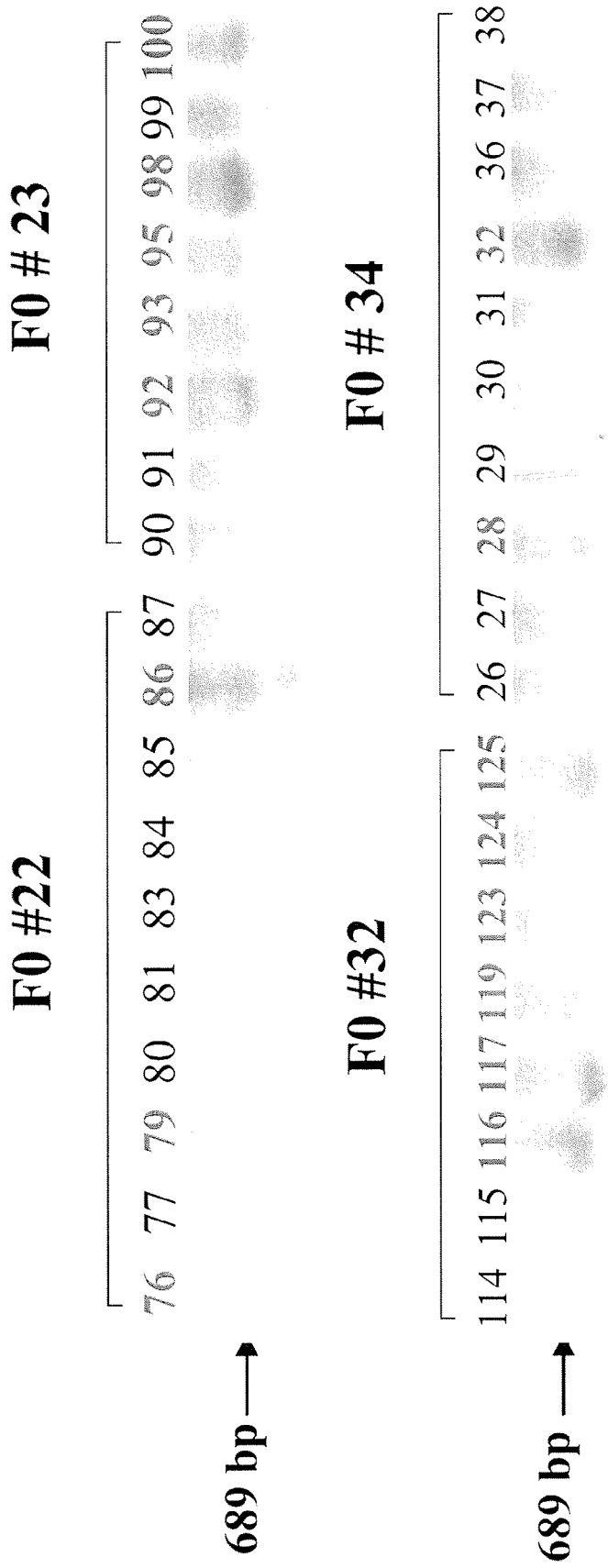
FIG. 14 shows the transmission of exogenous DNA to subsequent generations of transgenic chicken. The results of Southern-blot analysis for the detection of human Interferon-β sequence (684 b.p.) in the genomic DNA from red blood cells of second generation (F1 progeny) transgenic chickens.

In another study, the presence of human interferon β transgene [SEQ ID NO:4] in red blood cells of F1 generation transgenic chicken was also examined. F0 transgenic hens obtained as described above, were randomly selected and mated with wild type roosters. F1 offspring were generated from these matings and blood from the F1 transgenic chickens were collected and assayed for the presence of human interferon β gene using Southern Blot analysis. As shown in FIG. 19, transgenic F0 hen #22 transmitted the human interferon β gene to 3 offspring (indicated in FIG. 13 as lanes 76, 79 and 86); F0 hen #23 transmitted human interferon β gene to F1 offspring (indicated in FIG. 14 as lanes 92, 93, 95, 98 and 100); F0 hen #32 transmitted the exogenous DNA (transgene human interferon β) to F1 offspring (indicated as 116, 117, 119, 123, 124 and 125); and F0 hen #34 transmitted the transgene to F1 offspring indicated as 28 and 32). Thus, the human interferon β gene was integrated stably into the chicken genome and was transferred to subsequent transgenic generations.

Figure 15:
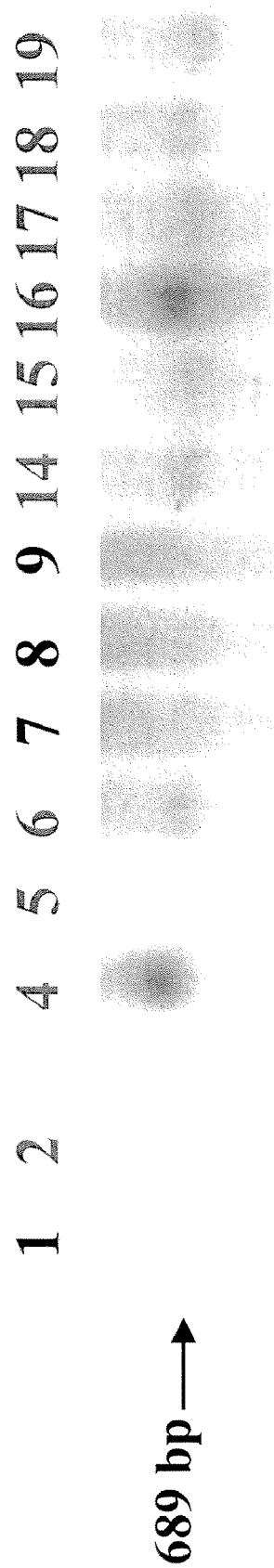
FIG. 15 shows the results of Southern-blot analysis for the detection of human Interferon-β sequence (684 b.p.) in the genomic DNA from red blood cells of third generation (F2 progeny) transgenic chickens. The F2 progeny were obtained from mating F1 transgenic hen with wild type rooster.

The stable integration and transmission of the human interferon β transgene to further generations of offspring was also observed. F1 transgenic hen were randomly selected and mated with wild type roosters. The presence of the human interferon-β gene in the F2 progeny was then detected using Southern blot analysis. As shown in FIG. 15, transgenic F1 hen 28 (which is the offspring of F0 34 hen) transmitted the exogenous DNA to 10F2 offspring (indicated in FIG. 20 as lanes 2, 4, 5, 6, 14, 15, 16, 17, 18 and 19).

The preceding examples demonstrate that the inventor has produced a number of genetically modified animals wherein the transgene is stably integrated into the genome of subsequent generations using the sperm vectors as described above. These data are intended only as examples and are not intended to limit the invention to these examples. It is understood that modifying the examples does not depart from the spirit of the invention.

What is claimed is:

1. A sperm-linker-DNA complex comprising:
   a) a sperm cell
   b) at least one anti-sperm monoclonal antibody linker, wherein the anti-sperm monoclonal antibody linker does not inhibit fertilization, and wherein said monoclonal antibody linker specifically binds sperm cells; and
   c) at least one DNA molecule;
   wherein fertilization of an oocyte by the sperm-linker-DNA complex can effectuate fertilization of an oocyte and introduce the DNA molecule into the oocyte.

2. The sperm-linker-DNA complex of claim 1, wherein the DNA molecule is a gene.

3. The sperm-linker-DNA complex of claim 2, wherein the DNA molecule encodes an anti-sense RNA molecule to inhibit translation and production of a preselected protein.

4. The sperm-linker-DNA complex of claim 2, wherein the gene encodes a preselected protein.

5. The sperm-linker-DNA complex of claim 3, wherein the preselected protein is implicated in a disease.

6. The sperm-linker-DNA complex of claim 4, wherein the preselected protein has anti-inflammatory, antiviral or anti-cancer activity.

* * * * *